WO 2006/103429 A2 10/2006
WO WO 2017/163064 A1 9/2017
WO WO 2018/073595 A1 4/2018

US012103971B2

(12) United States Patent
Dembek et al.

(10) Patent No.: US 12,103,971 B2
(45) Date of Patent: Oct. 1, 2024

(54) HIV SPECIFIC BINDING MOLECULES

(71) Applicant: Immunocore Limited, Abingdon (GB)

(72) Inventors: Marcin Dembek, Abingdon (GB); Luis Filipe Da Silva Godinho, Abingdon (GB); Praveen Singh, Abingdon (GB); Emma Elizabeth Baston, Abingdon (GB); Andrew Creese, Abingdon (GB); Thomas Minshull, Abingdon (GB); Pranav Bheamadu, Abingdon (GB)

(73) Assignee: IMMUNOCORE LIMITED, Abingdon (GB)

( * ) Notice: Subject to any disclaimer, the term of this patent is extended or adjusted under 35 U.S.C. 154(b) by 0 days.

(21) Appl. No.: 17/938,321

(22) Filed: Oct. 5, 2022

(65) Prior Publication Data
US 2023/0265191 A1 Aug. 24, 2023

Related U.S. Application Data

(60) Provisional application No. 63/312,077, filed on Feb. 20, 2022.

(51) Int. Cl.
| C07K 16/28 | (2006.01) |
| A61K 47/64 | (2017.01) |
| A61P 31/18 | (2006.01) |
| C07K 14/725 | (2006.01) |
| A61K 38/00 | (2006.01) |

(52) U.S. Cl.
CPC ...... *C07K 16/2809* (2013.01); *A61K 47/6425* (2017.08); *A61P 31/18* (2018.01); *C07K 14/7051* (2013.01); *A61K 38/00* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 8,378,074 B2 | 2/2013 | Jakobsen et al. |
| 8,519,100 B2 | 8/2013 | Jakobsen et al. |
| 9,068,178 B2 | 6/2015 | Jakobsen et al. |
| 9,255,135 B2 | 2/2016 | Jakobsen et al. |
| 11,440,944 B2 | 9/2022 | Mahon et al. |
| 2023/0192806 A1 | 6/2023 | Mahon et al. |

FOREIGN PATENT DOCUMENTS

| CN | 101155829 A | 4/2008 |
| CN | 104017067 A | 9/2014 |
| CN | 106478807 A | 3/2017 |
| JP | 2008-535826 A | 9/2008 |
| WO | WO 2005/113595 A2 | 12/2005 |
| WO | WO 2005/114215 A2 | 12/2005 |
| WO | WO 2006/103429 A2 | 10/2006 |
| WO | WO 2017/163064 A1 | 9/2017 |
| WO | WO 2018/073595 A1 | 4/2018 |

OTHER PUBLICATIONS

Bragado et al., "Allelic polymorphism in the coding region of human TCR Cα gene and characterization of structural variability in the a chain constant domain," *International Immunology*, vol. 6, Issue 2, Feb. 1994, pp. 223-230.

Foote and Winter, "Antibody framework residues affecting the conformation of the hypervariable loops," *Journal of Molecular Biology*, vol. 224, Issue 2, Mar. 20, 1992, pp. 487-499, https://doi.org/10.1016/0022-2836(92)91010-M.

International Preliminary Report on Patentability, Chapter 1, Patent Cooperation Treaty Application No. PCT/GB2017/050805, Sep. 25, 2018, 6 pages.

International Search Report and Written Opinion, PCT Application No. PCT/GB2017/050805, Jun. 21, 2017, 11 pages.

Rolland et al., "Broad and Gag-Biased HIV-1 Epitope Repertoires Are Associated with Lower Viral Loads," *PLoS One*, Jan. 2008, 3(1): e1424, 6 pages.

Rosenberg et al., "Adoptive cell transfer: a clinical path to effective cancer immunotherapy," *Nature Reviews Cancer*, Apr. 2008, 8(4):299-308.

Sewell et al., "Antagonism of cytotoxic T lymphocyte-mediated lysis by natural HIV-1 altered peptide ligands requires simultaneous presentation of agonist and antagonist peptides," *European Journal of Immunology*, Sep. 1997, vol. 27, Issue 9, pp. 2323-2329.

Varela-Rohena, A. et al., "Control of HIV-1 immune escape by CD8 T cells expressing enhanced T-cell receptor," *nature medicine*, Dec. 2008, vol. 14, No. 12, pp. 1390-1395.

Winter and Harris, "Humanized antibodies," *Immunology Today*, vol. 14, Issue 6, Jun. 1993, pp. 243-246, https://doi.org/10.1016/0167-5699(93)90039-N.

Lefranc, M., et al., The T Cell Receptor FactsBook, 2001, Academic Press, ISBN 0-12-441352- 8, pp. 76-77 and 188-191.

International Search Report and Written Opinion, PCT Application No. PCT/GB2023/054236, May 26, 2023, 16 pages.

Laugel, Bruno, et al., "Design of Soluble Recombinant T Cell Receptors for Antigen Targeting and T Cell Inhibition," *The Journal of Biological Chemistry*, vol. 280, Issue 3, Jan. 2005, pp. 1882-1892, DOI:https://doi.org/10.1074/jbc.M409427200.

Aggen, D. H., et al., "Identification and engineering of human variable regions that allow expression of stable single-chain T cell receptors," *Protein Engineering, Design & Selection*, vol. 24, Issue 4, Apr. 2011, pp. 361-372, https://doi.org/10.1093/protein/gzq113.

(Continued)

*Primary Examiner* — Meera Natarajan
*Assistant Examiner* — Cheom-Gil Cheong
(74) *Attorney, Agent, or Firm* — Fenwick & West LLP

(57) ABSTRACT

Specific binding molecules, including T cell receptors (TCRs), which bind the HLA-A*02 restricted peptide SLYNTVATL (SEQ ID NO: 1) derived from the HIV Gag gene product, p17 are presented. TCRs of the present invention comprise non-natural mutations within the alpha and/or beta variable domains relative to a native TCR. The specific binding molecules of the invention have improved stability and/or yield and yet unexpectedly retain the advantageous properties of the specific binding molecules from which they are derived. Such specific binding molecules are particularly useful in the development of soluble immunotherapeutic reagents for the treatment of HIV infected individuals.

16 Claims, 4 Drawing Sheets

Specification includes a Sequence Listing.

(56) References Cited

OTHER PUBLICATIONS

Schiffter, H.A., "Pharmaceutical Proteins—Structure, Stability, and Formulation," Reference Module in Biomedical Sciences, Comprehensive Biotechnology (Second Edition), vol. 5, 2011, pp. 521-541, https://doi.org/10.1016/B978-0-08-088504-9.00468-2.

Figure 1A

*Amino acid sequence of TCR alpha and beta chain variable regions*

Alpha

AKEVEQNSGP LSVPEGAIAS LNCTYSSWEG QSFFWYRQYS GKSPELIMFL YADPDKEDGR
FTAQLNKASQ YVSLLIRDSQ PSDSATYLCA VRTNSGYALN FGKGTSLLVT P (SEQ ID NO: 33)

Beta

DAGVTQSPTH LIKTRGQQVT LRCSPKSGHD TVSWYQQALG QGPQFIFQAV RGVERQRGNF
PDRFSGHQFP NYSSELNVNA LLLGDSALYL CASSDTVSYE QYFGPGTRLT VT (SEQ ID NO: 34)

Figure 1B

*Amino acid sequence of bispecific protein*

Alpha

AKEVEQNSGP LSVPEGAIAS LNCTYSSWEG QSFFWYRQYS GKSPELIMFL YADPDKEDGR
FTAQLNKASQ YVSLLIRDSQ PSDSATYLCA VRTNSGYALN FGKGTSLLVT PHIQKPDPAV
YQLRDSKSSD KSVCLFTDFD SQTNVSQSKD SDVYITDKCV LDMRSMDFKS NSAVAWSNKS
DFACANAFNN SIIPEDT (SEQ ID NO: 35)

Beta

AIQMTQSPSS LSASVGDRVT ITCRASQDIR NYLNWYQQKP GKAPKLLIYY TSRLESGVPS
RFSGSGSGTD YTLTISSLQP EDFATYYCQQ GNTLPWTFGQ GTKVEIKGGG GSGGGGSGGG
GSGGGGSGGG SEVQLVESGG GLVQPGGSLR LSCAASGYSF TGYTMNWVRQ APGKGLEWVA
LINPYKGVST YNQKFKDRFT ISVDKSKNTA YLQMNSLRAE DTAVYYCARS GYYGDSDWYF
DVWGQGTLVT VSSGGGGSDA GVTQSPTHLI KTRGQQVTLR CSPKSGHDTV SWYQQALGQG
PQFIFQAVRG VERQRGNFPD RFSGHQFPNY SSELNVNALL LGDSALYLCA SSDTVSYEQY
FGPGTRLTVT EDLKNVFPPE VAVFEPSEAE ISHTQKATLV CLATGFYPDH VELSWWVNGK
EVHSGVCTDP QPLKEQPALN DSRYALSSRL RVSATFWQDP RNHFRCQVQF YGLSENDEWT
QDRAKPVTQI VSAEAWGRAD (SEQ ID NO: 36)

Figure 2

*Amino acid sequence of TCR alpha chain variable region, with F50K mutation double underlined*

AKEVEQNSGP LSVPEGAIAS LNCTYSSWEG QSFFWYRQYS GKSPELIMKL YADPDKEDGR
FTAQLNKASQ YVSLLIRDSQ PSDSATYLCA VRTNSGYALN FGKGTSLLVT P (SEQ ID NO: 2)

*Yield of bispecific protein per volume of culture*

*Binding kinetics for M49K and F50K mutants*

Figure 5

*Amino acid sequence of TCR alpha chain variable region, with F50K and S96A mutations double underlined*

AKEVEQNSGP LSVPEGAIAS LNCTYSSWEG QSFFWYRQYS GKSPELIMKL YADPDKEDGR
FTAQLNKASQ YVSLLIRDSQ PSDSATYLCA VRTNAGYALN FGKGTSLLVT P (SEQ ID NO: 4)

Figure 6

*Amino acid sequence F50K + S96A of a bispecific protein comprising F to K and S to A mutations in the alpha chain variable region and alternative antiCD3*

Alpha
AKEVEQNSGP LSVPEGAIAS LNCTYSSWEG QSFFWYRQYS GKSPELIMKL YADPDKEDGR
FTAQLNKASQ YVSLLIRDSQ PSDSATYLCA VRTNAGYALN FGKGTSLLVT PHIQKPDPAV
YQLRDSKSSD KSVCLFTDFD SQTNVSQSKD SDVYITDKCV LDMRSMDFKS NSAVAWSNKS
DFACANAFNN SIIPEDT (SEQ ID NO: 32)

Beta
AIQMTQSPSS LSASVGDRVT ITCRASQDIR NYLNWYQQKP GKAPKLLIYY TSRLESGVPS
RFSGSGSGTD YTLTISSLQP EDFATYYCQQ GNTLPWTFGQ GTKVEIKGGG GSGGGGSGGG
GSGGGGSGGG SEVQLVESGG GLVQPGGSLR LSCAASGYSF TGYAMNWVRQ APGKGLEWVA
LINPYKGVST YNQKFKDRFT FSVDKSKNTA YLQMNSLRAE DTAVYYCARS GYYGDSDWYF
DVWGQGTLVT VSSGGGGSDA GVTQSPTHLI KTRGQQVTLR CSPKSGHDTV SWYQQALGQG
PQFIFQAVRG VERQRGNFPD RFSGHQFPNY SSELNVNALL LGDSALYLCA SSDTVSYEQY
FGPGTRLTVT EDLKNVFPPE VAVFEPSEAE ISHTQKATLV CLATGFYPDH VELSWWVNGK
EVHSGVCTDP QPLKEQPALN DSRYALSSRL RVSATFWQDP RNHFRCQVQF YGLSENDEWT
QDRAKPVTQI VSAEAWGRAD (SEQ ID NO: 30)

*Potency of T cell redirection as determined by IFNγ (upper) and GrB (lower) release*

SEQUENCE LISTING

```
Sequence total quantity: 50
SEQ ID NO: 1                  moltype = AA    length = 9
FEATURE                       Location/Qualifiers
source                        1..9
                              mol_type = protein
                              organism = Human immunodeficiency virus 1
SEQUENCE: 1
SLYNTVATL                                                                       9

SEQ ID NO: 2                  moltype = AA    length = 111
FEATURE                       Location/Qualifiers
source                        1..111
                              mol_type = protein
                              organism = synthetic construct
REGION                        1..111
                              note = Description of Artificial Sequence:
                              Syntheticpolypeptide
SEQUENCE: 2
AKEVEQNSGP LSVPEGAIAS LNCTYSSWEG QSFFWYRQYS GKSPELIMKL YADPDKEDGR               60
FTAQLNKASQ YVSLLIRDSQ PSDSATYLCA VRTNSGYALN FGKGTSLLVT P                        111

SEQ ID NO: 3                  moltype = AA    length = 111
FEATURE                       Location/Qualifiers
source                        1..111
                              mol_type = protein
                              organism = synthetic construct
REGION                        1..111
                              note = Description of Artificial Sequence:
                              Syntheticpolypeptide
SEQUENCE: 3
AKEVEQNSGP LSVPEGAIAS LNCTYSSWEG QSFFWYRQYS GKSPELIMFL YADPDKEDGR               60
FTAQLNKASQ YVSLLIRDSQ PSDSATYLCA VRTNAGYALN FGKGTSLLVT P                        111

SEQ ID NO: 4                  moltype = AA    length = 111
FEATURE                       Location/Qualifiers
source                        1..111
                              mol_type = protein
                              organism = synthetic construct
REGION                        1..111
                              note = Description of Artificial Sequence:
                              Syntheticpolypeptide
SEQUENCE: 4
AKEVEQNSGP LSVPEGAIAS LNCTYSSWEG QSFFWYRQYS GKSPELIMKL YADPDKEDGR               60
FTAQLNKASQ YVSLLIRDSQ PSDSATYLCA VRTNAGYALN FGKGTSLLVT P                        111

SEQ ID NO: 5                  moltype = AA    length = 112
FEATURE                       Location/Qualifiers
source                        1..112
                              mol_type = protein
                              organism = synthetic construct
REGION                        1..112
                              note = Description of Artificial Sequence:
                              Syntheticpolypeptide
SEQUENCE: 5
DAGVTQSPTH LIKTRGQQVT LRCSPKSGHD TVSWYQQALG QGPQFIFQAV RGVERQRGNF               60
PDRFSGHQFP NYSSELNVNA LLLGDSALYL CASSDTVSYE QYFGPGTRLT VT                       112

SEQ ID NO: 6                  moltype = AA    length = 9
FEATURE                       Location/Qualifiers
source                        1..9
                              mol_type = protein
                              organism = Human immunodeficiency virus 1
SEQUENCE: 6
SLFNTVATL                                                                       9

SEQ ID NO: 7                  moltype = AA    length = 9
FEATURE                       Location/Qualifiers
source                        1..9
                              mol_type = protein
                              organism = Human immunodeficiency virus 1
SEQUENCE: 7
SLFNTVAVL                                                                       9

SEQ ID NO: 8                  moltype = AA    length = 9
FEATURE                       Location/Qualifiers
source                        1..9
                              mol_type = protein
                              organism = Human immunodeficiency virus 1
```

```
SEQUENCE: 8
SLSNTVATL                                                                                   9

SEQ ID NO: 9            moltype = AA  length = 9
FEATURE                 Location/Qualifiers
source                  1..9
                        mol_type = protein
                        organism = Human immunodeficiency virus 1
SEQUENCE: 9
SSFNTVATL                                                                                   9

SEQ ID NO: 10           moltype = AA  length = 9
FEATURE                 Location/Qualifiers
source                  1..9
                        mol_type = protein
                        organism = Human immunodeficiency virus 1
SEQUENCE: 10
SLLNTVATL                                                                                   9

SEQ ID NO: 11           moltype = AA  length = 9
FEATURE                 Location/Qualifiers
source                  1..9
                        mol_type = protein
                        organism = Human immunodeficiency virus 1
SEQUENCE: 11
SLYNTIATL                                                                                   9

SEQ ID NO: 12           moltype = AA  length = 9
FEATURE                 Location/Qualifiers
source                  1..9
                        mol_type = protein
                        organism = Human immunodeficiency virus 1
SEQUENCE: 12
SLYNTIAVL                                                                                   9

SEQ ID NO: 13           moltype = AA  length = 9
FEATURE                 Location/Qualifiers
source                  1..9
                        mol_type = protein
                        organism = Human immunodeficiency virus 1
SEQUENCE: 13
SLFNTIATL                                                                                   9

SEQ ID NO: 14           moltype = AA  length = 9
FEATURE                 Location/Qualifiers
source                  1..9
                        mol_type = protein
                        organism = Human immunodeficiency virus 1
SEQUENCE: 14
SLFNTIAVL                                                                                   9

SEQ ID NO: 15           moltype = AA  length = 9
FEATURE                 Location/Qualifiers
source                  1..9
                        mol_type = protein
                        organism = Human immunodeficiency virus 1
SEQUENCE: 15
SLYNFVAVL                                                                                   9

SEQ ID NO: 16           moltype = AA  length = 5
FEATURE                 Location/Qualifiers
source                  1..5
                        mol_type = protein
                        organism = synthetic construct
REGION                  1..5
                        note = Description of Artificial Sequence: Syntheticpeptide
SEQUENCE: 16
GGGGS                                                                                       5

SEQ ID NO: 17           moltype = AA  length = 5
FEATURE                 Location/Qualifiers
source                  1..5
                        mol_type = protein
                        organism = synthetic construct
REGION                  1..5
                        note = Description of Artificial Sequence: Syntheticpeptide
SEQUENCE: 17
GGGSG                                                                                       5
```

| | | |
|---|---|---|
| SEQ ID NO: 18<br>FEATURE<br>source<br><br>REGION<br><br>SEQUENCE: 18<br>GGSGG | moltype = AA  length = 5<br>Location/Qualifiers<br>1..5<br>mol_type = protein<br>organism = synthetic construct<br>1..5<br>note = Description of Artificial Sequence: Syntheticpeptide | <br><br><br><br><br><br><br>5 |
| SEQ ID NO: 19<br>FEATURE<br>source<br><br>REGION<br><br>SEQUENCE: 19<br>GSGGG | moltype = AA  length = 5<br>Location/Qualifiers<br>1..5<br>mol_type = protein<br>organism = synthetic construct<br>1..5<br>note = Description of Artificial Sequence: Syntheticpeptide | <br><br><br><br><br><br><br>5 |
| SEQ ID NO: 20<br>FEATURE<br>source<br><br>REGION<br><br>SEQUENCE: 20<br>GSGGGP | moltype = AA  length = 6<br>Location/Qualifiers<br>1..6<br>mol_type = protein<br>organism = synthetic construct<br>1..6<br>note = Description of Artificial Sequence: Syntheticpeptide | <br><br><br><br><br><br><br>6 |
| SEQ ID NO: 21<br>FEATURE<br>source<br><br>REGION<br><br>SEQUENCE: 21<br>GGEPS | moltype = AA  length = 5<br>Location/Qualifiers<br>1..5<br>mol_type = protein<br>organism = synthetic construct<br>1..5<br>note = Description of Artificial Sequence: Syntheticpeptide | <br><br><br><br><br><br><br>5 |
| SEQ ID NO: 22<br>FEATURE<br>source<br><br>REGION<br><br>SEQUENCE: 22<br>GGEGGGP | moltype = AA  length = 7<br>Location/Qualifiers<br>1..7<br>mol_type = protein<br>organism = synthetic construct<br>1..7<br>note = Description of Artificial Sequence: Syntheticpeptide | <br><br><br><br><br><br><br>7 |
| SEQ ID NO: 23<br>FEATURE<br>source<br><br>REGION<br><br>SEQUENCE: 23<br>GGEGGGSEGG GS | moltype = AA  length = 12<br>Location/Qualifiers<br>1..12<br>mol_type = protein<br>organism = synthetic construct<br>1..12<br>note = Description of Artificial Sequence: Syntheticpeptide | <br><br><br><br><br><br><br>12 |
| SEQ ID NO: 24<br>FEATURE<br>source<br><br>REGION<br><br>SEQUENCE: 24<br>GGGSGGGG | moltype = AA  length = 8<br>Location/Qualifiers<br>1..8<br>mol_type = protein<br>organism = synthetic construct<br>1..8<br>note = Description of Artificial Sequence: Syntheticpeptide | <br><br><br><br><br><br><br>8 |
| SEQ ID NO: 25<br>FEATURE<br>source<br><br>REGION<br><br>SEQUENCE: 25<br>GGGS | moltype = AA  length = 4<br>Location/Qualifiers<br>1..4<br>mol_type = protein<br>organism = synthetic construct<br>1..4<br>note = Description of Artificial Sequence: Syntheticpeptide | <br><br><br><br><br><br><br>4 |

```
SEQ ID NO: 26              moltype = AA  length = 5
FEATURE                    Location/Qualifiers
source                     1..5
                           mol_type = protein
                           organism = synthetic construct
REGION                     1..5
                           note = Description of Artificial Sequence: Syntheticpeptide
SEQUENCE: 26
GGGGS                                                                              5

SEQ ID NO: 27              moltype = AA  length = 5
FEATURE                    Location/Qualifiers
source                     1..5
                           mol_type = protein
                           organism = synthetic construct
REGION                     1..5
                           note = Description of Artificial Sequence: Syntheticpeptide
SEQUENCE: 27
TVLRT                                                                              5

SEQ ID NO: 28              moltype = AA  length = 6
FEATURE                    Location/Qualifiers
source                     1..6
                           mol_type = protein
                           organism = synthetic construct
REGION                     1..6
                           note = Description of Artificial Sequence: Syntheticpeptide
SEQUENCE: 28
TVSSAS                                                                             6

SEQ ID NO: 29              moltype = AA  length = 7
FEATURE                    Location/Qualifiers
source                     1..7
                           mol_type = protein
                           organism = synthetic construct
REGION                     1..7
                           note = Description of Artificial Sequence: Syntheticpeptide
SEQUENCE: 29
TVLSSAS                                                                            7

SEQ ID NO: 30              moltype = AA  length = 500
FEATURE                    Location/Qualifiers
source                     1..500
                           mol_type = protein
                           organism = synthetic construct
REGION                     1..500
                           note = Description of Artificial Sequence:
                           Syntheticpolypeptide
SEQUENCE: 30
AIQMTQSPSS LSASVGDRVT ITCRASQDIR NYLNWYQQKP GKAPKLLIYY TSRLESGVPS                  60
RFSGSGSGTD YTLTISSLQP EDFATYYCQQ GNTLPWTFGQ GTKVEIKGGG GSGGGGSGGG                  120
GSGGGGSGGG SEVQLVESGG GLVQPGGSLR LSCAASGYSF TGYAMNWVRQ APGKGLEWVA                  180
LINPYKGVST YNQKFKDRFT FSVDKSKNTA YLQMNSLRAE DTAVYYCARS GYYGDSDWYF                  240
DVWGQGTLVT VSSGGGSDA GVTQSPTHLI KTRGQQVTLR CSPKSGHDTV SWYQQALGQG                   300
PQFIFQAVRG VERQRGNFPD RFSGHQFPNY SSELNVNALL LGDSALYLCA SSDTVSYEQY                  360
FGPGTRLTVT EDLKNVFPPE VAVFEPSEAE ISHTQKATLV CLATGFYPDH VELSWWVNGK                  420
EVHSGVCTDP QPLKEQPALN DSRYALSSRL RVSATFWQDP RNHFRCQVQF YGLSENDEWT                  480
QDRAKPVTQI VSAEAWGRAD                                                              500

SEQ ID NO: 31              moltype = AA  length = 500
FEATURE                    Location/Qualifiers
source                     1..500
                           mol_type = protein
                           organism = synthetic construct
REGION                     1..500
                           note = Description of Artificial Sequence:
                           Syntheticpolypeptide
SEQUENCE: 31
AIQMTQSPSS LSASVGDRVT ITCRASQDIR NYLNWYQQKP GKAPKLLIYY TSRLESGVPS                  60
RFSGSGSGTD YTLTISSLQP EDFATYYCQQ GNTLPWTFGQ GTKVEIKGGG GSGGGGSGGG                  120
GSGGGGSGGG SEVQLVESGG GLVQPGGSLR LSCAASGYSF TGYAMNWVRQ APGKGLEWVA                  180
LINPYKGVST YNQKFKDRFT FSVDKSKNTA YLQMNSLRAE DTAVYYCARS GYYGDSDWYF                  240
DVWGQGTLVT VSSGGGSDA GVTQSPTHLI KTRGQQVTLR CSPKSGHDTV SWYQQALGQG                   300
PQFIFQAVRG VERQRGNFPD RFSGHQFPNY SSELNVNALL LGDSALYLCA SSDTVSYEQY                  360
FGPGTRLTVT EDLKNVFPPE VAVFEPSEAE ISHTQKATLV CLATGFYPDH VELSWWVNGK                  420
EVHSGVCTDP QPLKEQPALN DSRYALSSRL RVSATFWQDP RNHFRCQVQF YGLSENDEWT                  480
QDRAKPVTQI VSAEAWGRAD                                                              500
```

```
SEQ ID NO: 32            moltype = AA   length = 197
FEATURE                  Location/Qualifiers
source                   1..197
                         mol_type = protein
                         organism = synthetic construct
REGION                   1..197
                         note = Description of Artificial Sequence:
                         Syntheticpolypeptide
SEQUENCE: 32
AKEVEQNSGP LSVPEGAIAS LNCTYSSWEG QSFFWYRQYS GKSPELIMKL YADPDKEDGR    60
FTAQLNKASQ YVSLLIRDSQ PSDSATYLCA VRTNAGYALN FGKGTSLLVT PHIQKPDPAV   120
YQLRDSKSSD KSVCLFTDFD SQTNVSQSKD SDVYITDKCV LDMRSMDFKS NSAVAWSNKS   180
DFACANAFNN SIIPEDT                                                  197

SEQ ID NO: 33            moltype = AA   length = 111
FEATURE                  Location/Qualifiers
source                   1..111
                         mol_type = protein
                         organism = synthetic construct
REGION                   1..111
                         note = Description of Artificial Sequence:
                         Syntheticpolypeptide
SEQUENCE: 33
AKEVEQNSGP LSVPEGAIAS LNCTYSSWEG QSFFWYRQYS GKSPELIMFL YADPDKEDGR    60
FTAQLNKASQ YVSLLIRDSQ PSDSATYLCA VRTNSGYALN FGKGTSLLVT P            111

SEQ ID NO: 34            moltype = AA   length = 112
FEATURE                  Location/Qualifiers
source                   1..112
                         mol_type = protein
                         organism = synthetic construct
REGION                   1..112
                         note = Description of Artificial Sequence:
                         Syntheticpolypeptide
SEQUENCE: 34
DAGVTQSPTH LIKTRGQQVT LRCSPKSGHD TVSWYQQALG QGPQFIFQAV RGVERQRGNF    60
PDRFSGHQFP NYSSELNVNA LLLGDSALYL CASSDTVSYE QYFGPGTRLT VT           112

SEQ ID NO: 35            moltype = AA   length = 197
FEATURE                  Location/Qualifiers
source                   1..197
                         mol_type = protein
                         organism = synthetic construct
REGION                   1..197
                         note = Description of Artificial Sequence:
                         Syntheticpolypeptide
SEQUENCE: 35
AKEVEQNSGP LSVPEGAIAS LNCTYSSWEG QSFFWYRQYS GKSPELIMFL YADPDKEDGR    60
FTAQLNKASQ YVSLLIRDSQ PSDSATYLCA VRTNSGYALN FGKGTSLLVT PHIQKPDPAV   120
YQLRDSKSSD KSVCLFTDFD SQTNVSQSKD SDVYITDKCV LDMRSMDFKS NSAVAWSNKS   180
DFACANAFNN SIIPEDT                                                  197

SEQ ID NO: 36            moltype = AA   length = 500
FEATURE                  Location/Qualifiers
source                   1..500
                         mol_type = protein
                         organism = synthetic construct
REGION                   1..500
                         note = Description of Artificial Sequence:
                         Syntheticpolypeptide
SEQUENCE: 36
AIQMTQSPSS LSASVGDRVT ITCRASQDIR NYLNWYQQKP GKAPKLLIYY TSRLESGVPS    60
RFSGSGSGTD YTLTISSLQP EDFATYYCQQ GNTLPWTFGQ GTKVEIKGGG GSGGGGSGGG   120
GSGGGGSGGG SEVQLVESGG GLVQPGGSLR LSCAASGYSF TGYTMNWVRQ APGKGLEWVA   180
LINPYKGVST YNQKFKDRFT ISVDKSKNTA YLQMNSLRAE DTAVYYCARS GYYGDSDWYF   240
DVWGQGTLVT VSSGGGGSDA GVTQSPTHLI KTRGQQVTLR CSPKSGHDTV SWYQQALGQG   300
PQFIFQAVRG VERQRGNFPD RFSGHQFPNY SSELNVNALL LGDSALYLCA SSDTVSYEQY   360
FGPGTRLTVT EDLKNVFPPE VAVFEPSEAE ISHTQKATLV CLATGFYPDH VELSWWVNGK   420
EVHSGVCTDP QPLKEQPALN DSRYALSSRL RVSATFWQDP RNHFRCQVQF YGLSENDEWT   480
QDRAKPVTQI VSAEAWGRAD                                               500

SEQ ID NO: 37            moltype = AA   length = 20
FEATURE                  Location/Qualifiers
source                   1..20
                         mol_type = protein
                         organism = unidentified
REGION                   1..20
                         note = Description of Unknown:Albumin binding domain
                         sequence
```

```
SEQUENCE: 37
QRLMEDICLP RWGCLWEDDF                                                        20

SEQ ID NO: 38           moltype = AA  length = 13
        FEATURE                 Location/Qualifiers
        source                  1..13
                                mol_type = protein
                                organism = synthetic construct
        REGION                  1..13
                                note = Description of Artificial Sequence: Syntheticpeptide
SEQUENCE: 38
CAVRTNSGYA LNF                                                               13

SEQ ID NO: 39           moltype = AA  length = 13
        FEATURE                 Location/Qualifiers
        source                  1..13
                                mol_type = protein
                                organism = synthetic construct
        REGION                  1..13
                                note = Description of Artificial Sequence: Syntheticpeptide
SEQUENCE: 39
CAVRTNAGYA LNF                                                               13

SEQ ID NO: 40           moltype = AA  length = 9
        FEATURE                 Location/Qualifiers
        source                  1..9
                                mol_type = protein
                                organism = Human immunodeficiency virus 1
SEQUENCE: 40
SLYNTVAVL                                                                     9

SEQ ID NO: 41           moltype = AA  length = 112
        FEATURE                 Location/Qualifiers
        source                  1..112
                                mol_type = protein
                                organism = synthetic construct
        REGION                  1..112
                                note = Description of Artificial Sequence:
                                 Syntheticpolypeptide
        SITE                    1
                                note = May or may not be present
SEQUENCE: 41
MAKEVEQNSG PLSVPEGAIA SLNCTYSSWE GQSFFWYRQY SGKSPELIMK LYADPDKEDG    60
RFTAQLNKAS QYVSLLIRDS QPSDSATYLC AVRTNSGYAL NFGKGTSLLV TP          112

SEQ ID NO: 42           moltype = AA  length = 112
        FEATURE                 Location/Qualifiers
        source                  1..112
                                mol_type = protein
                                organism = synthetic construct
        REGION                  1..112
                                note = Description of Artificial Sequence:
                                 Syntheticpolypeptide
        SITE                    1
                                note = May or may not be present
SEQUENCE: 42
MAKEVEQNSG PLSVPEGAIA SLNCTYSSWE GQSFFWYRQY SGKSPELIMF LYADPDKEDG    60
RFTAQLNKAS QYVSLLIRDS QPSDSATYLC AVRTNAGYAL NFGKGTSLLV TP          112

SEQ ID NO: 43           moltype = AA  length = 112
        FEATURE                 Location/Qualifiers
        source                  1..112
                                mol_type = protein
                                organism = synthetic construct
        REGION                  1..112
                                note = Description of Artificial Sequence:
                                 Syntheticpolypeptide
        SITE                    1
                                note = May or may not be present
SEQUENCE: 43
MAKEVEQNSG PLSVPEGAIA SLNCTYSSWE GQSFFWYRQY SGKSPELIMK LYADPDKEDG    60
RFTAQLNKAS QYVSLLIRDS QPSDSATYLC AVRTNAGYAL NFGKGTSLLV TP          112

SEQ ID NO: 44           moltype = AA  length = 113
        FEATURE                 Location/Qualifiers
        source                  1..113
                                mol_type = protein
                                organism = synthetic construct
SEQUENCE: 44
```

```
MDAGVTQSPT HLIKTRGQQV TLRCSPKSGH DTVSWYQQAL GQGPQFIFQA VRGVERQRGN    60
FPDRFSGHQF PNYSSELNVN ALLLGDSALY LCASSDTVSY EQYFGPGTRL TVT          113

SEQ ID NO: 45            moltype = AA   length = 6
FEATURE                  Location/Qualifiers
source                   1..6
                         mol_type = protein
                         organism = synthetic construct
SEQUENCE: 45
SWEGQS                                                              6

SEQ ID NO: 46            moltype = AA   length = 6
FEATURE                  Location/Qualifiers
source                   1..6
                         mol_type = protein
                         organism = synthetic construct
SEQUENCE: 46
LYADPD                                                              6

SEQ ID NO: 47            moltype = AA   length = 13
FEATURE                  Location/Qualifiers
source                   1..13
                         mol_type = protein
                         organism = synthetic construct
SEQUENCE: 47
CAVRTNAGYA LNF                                                      13

SEQ ID NO: 48            moltype = AA   length = 5
FEATURE                  Location/Qualifiers
source                   1..5
                         mol_type = protein
                         organism = synthetic construct
SEQUENCE: 48
SGHDT                                                               5

SEQ ID NO: 49            moltype = AA   length = 6
FEATURE                  Location/Qualifiers
source                   1..6
                         mol_type = protein
                         organism = synthetic construct
SEQUENCE: 49
AVRGVE                                                              6

SEQ ID NO: 50            moltype = AA   length = 13
FEATURE                  Location/Qualifiers
source                   1..13
                         mol_type = protein
                         organism = synthetic construct
SEQUENCE: 50
CASSDTVSYE QYF                                                      13
```

HIV SPECIFIC BINDING MOLECULES

CROSS REFERENCE TO RELATED APPLICATIONS

This application claims the benefit of U.S. Provisional Application No. 63/312,077, filed Feb. 20, 2022, which is hereby incorporated in its entirety by reference.

SEQUENCE LISTING

The instant application contains a Sequence Listing which has been submitted electronically in XML format and is hereby incorporated by reference in its entirety. Said XML copy, created on Oct. 26, 2023, is named 33308-52639 US and is 61,321 bytes in size.

SUMMARY

The present invention relates to specific binding molecules, such as T cell receptors (TCRs), which bind the HLA-A*02 restricted peptide SLYNTVATL (SEQ ID NO: 1) derived from the HIV Gag gene product, p17. Said specific binding molecules may comprise CDR sequences embedded within a framework sequence. The CDRs and framework sequences may correspond to a T cell receptor (TCR) variable domain and may further comprise non-natural mutations relative to a native TCR variable domain. The specific binding molecules of the invention have improved stability and/or yield and yet unexpectedly retain the advantageous properties of the specific binding molecules from which they are derived (high affinity, specificity and sensitivity for a complex of SEQ ID NO: 1 and HLA-A*02, and drive a particularly potent T cell response). Such specific binding molecules are particularly useful in the development of soluble immunotherapeutic reagents for the treatment of HIV infected individuals.

Disclosed herein are specific binding molecules having the property of binding to SLYNTVATL (SEQ ID NO: 1) in complex with HLA-A*02 and comprising a TCR alpha chain variable domain and a TCR beta chain variable domain, wherein the alpha chain variable domain comprises an amino acid sequence selected from:

```
(a)
                                     (SEQ ID NO: 2)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNSGYALN FGKGTSLLVT P;

(b)
                                     (SEQ ID NO: 3)
AKEVEQNSGP LSVPEGAIAS LNCTYSSWEG QSFFWYRQYS

GKSPELIMFL YADPDKEDGR FTAQLNKASQ YVSLLIRDSQ

PSDSATYLCA VRTNAGYALN FGKGTSLLVT P;
or (c)
                                     (SEQ ID NO: 4)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNAGYALN FGKGTSLLVT P;
``` optionally with an N-terminal methionine (SEQ ID NOS: 41-43), and the beta chain variable domain comprises the amino acid sequence:

```
                                     (SEQ ID NO: 5)
DAGVTQSPTH LIKTRGQQVT LRCSPKSGHD TVSWYQQALG

QGPQFIFQAV RGVERQRGNF PDRFSGHQFP NYSSELNVNA

LLLGDSALYL CASSDTVSYE QYFGPGTRLT VT,
``` optionally with an N-terminal methionine (SEQ ID NO: 44).

In some embodiments, specific binding molecules have the property of binding to SLYNTVATL (SEQ ID NO: 1) in complex with HLA-A*02 and comprise a TCR alpha chain variable domain and a TCR beta chain variable domain, wherein the alpha chain variable domain has an amino acid sequence selected from:

```
(a)
                                     (SEQ ID NO: 2)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNSGYALN FGKGTSLLVT P;

(b)
                                     (SEQ ID NO: 3)
AKEVEQNSGP LSVPEGAIAS LNCTYSSWEG QSFFWYRQYS

GKSPELIMFL YADPDKEDGR FTAQLNKASQ YVSLLIRDSQ

PSDSATYLCA VRTNAGYALN FGKGTSLLVT P;
or (c)
                                     (SEQ ID NO: 4)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNAGYALN FGKGTSLLVT P;
``` optionally with an N-terminal methionine (SEQ ID NOs: 41-43), and the beta chain variable domain has the amino acid sequence:

```
                                     (SEQ ID NO: 5)
DAGVTQSPTH LIKTRGQQVT LRCSPKSGHD TVSWYQQALG

QGPQFIFQAV RGVERQRGNF PDRFSGHQFP NYSSELNVNA

LLLGDSALYL CASSDTVSYE QYFGPGTRLT VT,
``` optionally with an N-terminal methionine:

```
                                    (SEQ ID NO: 44)
MDAGVTQSPT HLIKTRGQQV TLRCSPKSGH DTVSWYQQAL

GQGPQFIFQA VRGVERQRGN FPDRFSGHQF PNYSSELNVN

ALLLGDSALY LCASSDTVSY EQYFGPGTRL TVT.
```

In another aspect, disclosed herein are nucleic acid molecules encoding a TCR alpha chain and/or a TCR beta chain, wherein the TCR alpha chain comprises a variable domain amino acid sequence selected from:

(a)

(SEQ ID NO: 2)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNSGYALN FGKGTSLLVT P;

(b)

(SEQ ID NO: 3)
AKEVEQNSGP LSVPEGAIAS LNCTYSSWEG QSFFWYRQYS

GKSPELIMFL YADPDKEDGR FTAQLNKASQ YVSLLIRDSQ

PSDSATYLCA VRTNAGYALN FGKGTSLLVT P;
or (c)

(SEQ ID NO: 4)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNAGYALN FGKGTSLLVT P;

optionally with an N-terminal methionine (SEQ ID NOS: 41-43), and/or
the TCR beta chain comprises the variable domain amino acid sequence:

(SEQ ID NO: 5)
DAGVTQSPTH LIKTRGQQVT LRCSPKSGHD TVSWYQQALG

QGPQFIFQAV RGVERQRGNF PDRFSGHQFP NYSSELNVNA

LLLGDSALYL CASSDTVSYE QYFGPGTRLT VT_, optionally with an N-terminal methionine (SEQ ID NO: 44).

In some embodiments, nucleic acid molecules encode a TCR alpha chain and/or a TCR beta chain, wherein the TCR alpha chain has a variable domain amino acid sequence selected from:

(a)

(SEQ ID NO: 2)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNSGYALN FGKGTSLLVT P;

(b)

(SEQ ID NO: 3)
AKEVEQNSGP LSVPEGAIAS LNCTYSSWEG QSFFWYRQYS

GKSPELIMFL YADPDKEDGR FTAQLNKASQ YVSLLIRDSQ

PSDSATYLCA VRTNAGYALN FGKGTSLLVT P;
or (c)

(SEQ ID NO: 4)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNAGYALN FGKGTSLLVT P;

optionally with an N-terminal methionine (SEQ ID NOs: 41-43), and/or
the TCR beta chain has the variable domain amino acid sequence:

(SEQ ID NO: 5)
DAGVTQSPTH LIKTRGQQVT LRCSPKSGHD TVSWYQQALG

QGPQFIFQAV RGVERQRGNF PDRFSGHQFP NYSSELNVNA

LLLGDSALYL CASSDTVSYE QYFGPGTRLT VT, optionally with an N-terminal methionine (SEQ ID NO: 44).

In another aspect, disclosed herein are pharmaceutical compositions comprising a specific binding molecule having the property of binding to SLYNTVATL (SEQ ID NO: 1) in complex with HLA-A*02 and comprising a TCR alpha chain variable domain and a TCR beta chain variable domain, wherein the alpha chain variable domain amino acid sequence comprises an amino acid sequence selected from:

(a)

(SEQ ID NO: 2)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNSGYALN FGKGTSLLVT P;

(b)

(SEQ ID NO: 3)
AKEVEQNSGP LSVPEGAIAS LNCTYSSWEG QSFFWYRQYS

GKSPELIMFL YADPDKEDGR FTAQLNKASQ YVSLLIRDSQ

PSDSATYLCA VRTNAGYALN FGKGTSLLVT P;
or (c)

(SEQ ID NO: 4)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNAGYALN FGKGTSLLVT P;

optionally with an N-terminal methionine (SEQ ID NOs: 41-43), and
the beta chain variable domain comprises the amino acid sequence:

(SEQ ID NO: 5)
DAGVTQSPTH LIKTRGQQVT LRCSPKSGHD TVSWYQQALG

QGPQFIFQAV RGVERQRGNF PDRFSGHQFP NYSSELNVNA

LLLGDSALYL CASSDTVSYE QYFGPGTRLT VT, optionally with an N-terminal methionine (SEQ ID NO: 44).

In some embodiments, the pharmaceutical compositions comprise a TCR alpha chain variable domain and a TCR beta chain variable domain, wherein the alpha chain variable domain has a TCR alpha chain variable domain and a TCR beta chain variable domain, wherein the alpha chain variable domain has an amino acid sequence selected from:

(a)

(SEQ ID NO: 2)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNSGYALN FGKGTSLLVT P;

-continued (b)
```
                                                    (SEQ ID NO: 3)
AKEVEQNSGP LSVPEGAIAS LNCTYSSWEG QSFFWYRQYS

GKSPELIMFL YADPDKEDGR FTAQLNKASQ YVSLLIRDSQ

PSDSATYLCA VRTNAGYALN FGKGTSLLVT P;
or (c)
                                                    (SEQ ID NO: 4)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNAGYALN FGKGTSLLVT P;
```
optionally with an N-terminal methionine (SEQ ID NOs: 41-43), and
the beta chain variable domain has the amino acid sequence:

```
                                                    (SEQ ID NO: 5)
DAGVTQSPTH LIKTRGQQVT LRCSPKSGHD TVSWYQQALG

QGPQFIFQAV RGVERQRGNF PDRFSGHQFP NYSSELNVNA

LLLGDSALYL CASSDTVSYE QYFGPGTRLT VT,
```
optionally with an N-terminal methionine (SEQ ID NO: 44).

Also disclosed herein are methods of treating HIV infection or AIDS in a human subject, comprising administering a therapeutically effective amount of a specific binding molecule having the property of binding to SLYNTVATL (SEQ ID NO: 1) in complex with HLA-A*02 and comprising a TCR alpha chain variable domain and a TCR beta chain variable domain, wherein the alpha chain variable domain comprises an amino acid sequence selected from:

(a)
```
                                                    (SEQ ID NO: 2)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNSGYALN FGKGTSLLVT P;

(b)
                                                    (SEQ ID NO: 3)
AKEVEQNSGP LSVPEGAIAS LNCTYSSWEG QSFFWYRQYS

GKSPELIMFL YADPDKEDGR FTAQLNKASQ YVSLLIRDSQ

PSDSATYLCA VRTNAGYALN FGKGTSLLVT P;
or (c)
                                                    (SEQ ID NO: 4)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNAGYALN FGKGTSLLVT P;
```
optionally with an N-terminal methionine (SEQ ID NOs: 41-43), and
the beta chain variable domain comprises the amino acid sequence:

```
                                                    (SEQ ID NO: 5)
DAGVTQSPTH LIKTRGQQVT LRCSPKSGHD TVSWYQQALG

QGPQFIFQAV RGVERQRGNF PDRFSGHQFP NYSSELNVNA

LLLGDSALYL CASSDTVSYE QYFGPGTRLT VT,
```
optionally with an N-terminal methionine (SEQ ID NO: 44).

In some embodiments, the methods comprise administering a therapeutically effective amount of a specific binding molecule having the property of binding to SLYNTVATL (SEQ ID NO: 1) in complex with HLA-A*02 and comprising a TCR alpha chain variable domain and a TCR beta chain variable domain, wherein the alpha chain variable domain has an amino acid sequence selected from:

(a)
```
                                                    (SEQ ID NO: 2)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNSGYALN FGKGTSLLVT P;

(b)
                                                    (SEQ ID NO: 3)
AKEVEQNSGP LSVPEGAIAS LNCTYSSWEG QSFFWYRQYS

GKSPELIMFL YADPDKEDGR FTAQLNKASQ YVSLLIRDSQ

PSDSATYLCA VRTNAGYALN FGKGTSLLVT P;
or (c)
                                                    (SEQ ID NO: 4)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNAGYALN FGKGTSLLVT P;
```
optionally with an N-terminal methionine (SEQ ID NOs: 41-43), and
the beta chain variable has the amino acid sequence:

```
                                                    (SEQ ID NO: 5)
DAGVTQSPTH LIKTRGQQVT LRCSPKSGHD TVSWYQQALG

QGPQFIFQAV RGVERQRGNF PDRFSGHQFP NYSSELNVNA

LLLGDSALYL CASSDTVSYE QYFGPGTRLT VT,
```
optionally with an N-terminal methionine (SEQ ID NO: 44).

In yet another aspect, disclosed herein are cells comprising (a) a TCR expression vector which comprises nucleic acid as disclosed herein in a single open reading frame or two distinct open reading frames encoding the alpha chain and the beta chain respectively; or (b) a first expression vector which comprises nucleic acid encoding the alpha chain of a TCR as disclosed herein and a second expression vector which comprises nucleic acid encoding the beta chain of a TCR as disclosed herein.

In yet another aspect, disclosed herein are isolated or non-naturally occurring cells, especially T-cells that present a TCR as disclosed herein.

BACKGROUND TO THE INVENTION

The Human Immuno-deficiency Virus (HIV) is the causative agent of Acquired Immune Deficiency Syndrome (AIDS). The virus is an enveloped retrovirus belonging to the lentivirus group. In 2020 it was estimated that there were around 40 million adults & children living with HIV globally (AIDS by the Numbers. UNAIDS. 2020); Accessed Jun. 29, 2021. www.unaids.org.) Current treatments rely on the use of combination antiretroviral therapy (ART) to control viral infection. However, although effective, these treatments are unable to completely eradicate infection due to the stable integration of viral genes into host cell chromosomes, leading to the rapid establishment of a reservoir of long-lived, latently infected CD4+ T cells (Siliciano et al. 2003 Nat Med, 9, 727). Viral rebound typically occurs upon treatment cessation meaning that lifelong treatment is required. The majority of people living with HIV make vigorous T cell responses against HIV Gag proteins during the course of infection, yet these T cells are incapable of eliminating long-lived CD4+ T cells that harbor replication-competent proviruses. The immunotherapeutic strategies that have been tested to date have not yielded meaningful clinical benefits in terms of post-treatment control and/or reduction in HIV reservoirs. (Ward A R et al., Semin Immunol. 2020:101412. Barr L, et al., Journal of Virus Eradication. 2020:6:100010. Therefore, new treatments are required which have the potential to eradicate viral reservoirs and to achieve a functional cure.

A novel immunotherapeutic approach involves using engineered T cell receptors (TCRs) to generate a potent immune response against HIV infected cells. In nature. T cells and TCRs typically have a weak affinity for antigen, in the low micromolar to nanomolar range. Engineering the TCR by mutating the antigen recognition site can produce increases in antigen affinity which can lead to an enhanced immune response in vivo. In the context of HIV, the enhanced response should be sufficient to eradicate the replication competent virus from viral reservoirs with low level antigen expression. Such engineered TCRs may be used in cellular therapy applications with gene modified T cells (see Vonderheide and June, 2014, Immunol Rev, 257, 7-13). Alternatively, engineered TCRs may be produced as soluble reagents for the purpose of delivering cytotoxic or immuno-stimulatory agents to the infected cells (Lissin, et al., (2013). "High-Affinity Monocloncal T-cell receptor (mTCR) Fusions. Fusion Protein Technologies for Biopharmaceuticals: Applications and Challenges". S. R. Schmidt, Wiley: Boulter, et al., (2003). Protein Eng 16(9): 707-711: Liddy, et al., (2012), Nat Med 8: 980-987: WO03/020763). A similar approach has been successfully developed for treatment of certain cancers (Nathan, P. et al. New: Engl J Med 385, 1196-1206 (2021)).

For soluble TCRs to be used as therapeutics it is desirable that the affinity ($K_D$) and/or the binding half-life for antigen is particularly high, for example a $K_D$ in the picomolar range and/or a binding half-life of several hours. Such high affinities are required to drive a potent response against target cells presenting low levels of antigen. In all applications involving affinity engineered TCRs, it is essential that the TCRs not only have a higher affinity for antigen than the corresponding wild type TCR, but also retain a high level of antigen specificity. Loss of specificity in this context may result in off-target effects when such TCRs are administered to patients.

Affinity maturation typically involves the skilled person having to identify specific mutations and/or combinations of mutations, including but not limited to substitutions, insertions and/or deletions, that can be made to a WT TCR sequence in order to increase the strength of antigen recognition. Methods to identify mutations of a given TCR that confer an affinity enhancement are known in the art, for example the use of display libraries (Li et al., (2005) Nat Biotechnol. 23(3):349-354; Holler et al., (2000). Proc Natl Acad Sci USA: 97(10):5387-5392). However, to produce significant increases in the affinity of a given TCR against a given target requires the skilled person to select specific mutations and/or combinations of mutations from a large pool of possible alternatives. In many cases it may not be possible to achieve the desired affinity and specificity. The mutations required for high affinity and high specificity should also produce a TCR that is able to be expressed, refolded and purified at a reasonable yield and that is highly stable in a purified form.

The peptide sequence SLYNTVATL (SEQ ID NO 1) is derived from the p17 gene product of the Gag gene, one of nine genes which make up the HIV virus and to which T cell responses have been shown to be particularly effective in controlling viral load, indicating that this epitope is immunodominant (Rolland et al. 2008, PLOS One, 3:e1424; Streeck H, et al. J Virol. 2009:83(15): 7641-7648: Pereyra et al. J Virol. 2014:88(22): 12937-12948). The peptide (termed Gag herein) is presented by HLA-A*02 on the surface of HIV infected cells. Gag-specific T cells have also been detected in ART-treated (aviremic) individuals, albeit at lower frequencies (Gray C M, et al. J Immunol. 1999:162 (3): 1780-1788: Ogg G S, et al. J Virol. 1999:73(1): 797-800; Seth A, et al. J Infect Dis. 2001:183(5): 722-729) Therefore, the Gag-HLA-A*02 complex provides an ideal target for the TCR-based recognition of HIV infected cells.

WO 2017163064 discloses TCRs that have been mutated relative to a WT TCR that recognizes the Gag-HLA-A*02 complex. CD8+ cytotoxic T cells transduced with said affinity enhanced TCRs were able to control HIV infection in vitro at suitable effector target ratios for T cell therapy. These TCRs were able to recognize all of the most common viral escape peptides (Varela-Rohena et al. 2008, Nat Med, 14(12):1390-5). Such TCRs have utility in adoptive T cell therapy and well as in soluble TCR based therapeutics. Furthermore, Yang et al., describes in vivo studies showing that bispecific molecules incorporating the TCRs disclosed in WO2017163064 could eliminate HIV-infected CD4+ T cells from ART-treated individuals through redirection of polyclonal (non-HIV-specific) CD8+ T cells, bypassing HIV-specific immune effectors that may have become dysfunctional (Yang H, et al. Mol Ther. 2016:24(11): 1913-1925).

The inventors have found certain mutations of a TCR disclosed in WO 2017163064 can unexpectedly increase yield during production in *E. coli* and/or stability, without affecting target binding. Such molecules have ideal properties for clinical development.

BRIEF DESCRIPTION OF THE DRAWINGS

FIG. 1A shows the amino acid sequence of the TCR alpha and beta chain variable regions of a TCR disclosed in WO2017163064 and FIG. 1B shows the amino acid sequences of a bispecific protein disclosed in WO2017163064.

FIG. 2 shows the amino acid sequence of TCR alpha chain variable region of a specific binding molecule of the invention, with F50K mutation double underlined.

FIG. 5 shows the amino acid sequence of a TCR alpha chain variable region of a specific binding molecule of the invention, with F50K and S96A mutations double underlined.

FIG. 6 shows the amino acid sequences of a bispecific protein of the invention.

DETAILED DESCRIPTION OF THE INVENTION

Figure 3:
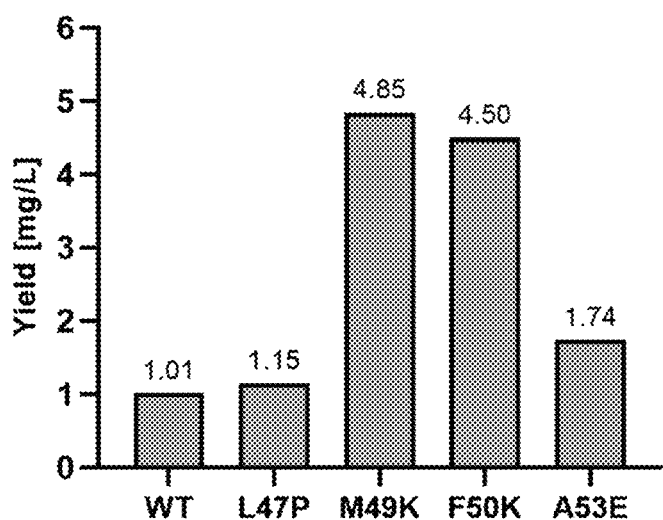
FIG. 3 is a graph showing the yield of bispecific proteins having different mutations therein, per volume of culture. The numeric position of the mutation as provided on the x-axis assumes the presence of the optional N-terminal methionine.

In a first aspect, the present invention provides a specific binding molecule having the property of binding to SLYN-TVATL (SEQ ID NO: 1) in complex with HLA-A*02 and comprising a TCR alpha chain variable domain and a TCR beta chain variable domain,
wherein the alpha chain variable domain comprises an amino acid sequence selected from:

(a)
(SEQ ID NO: 2)
<u>A</u>KEVEQNSGP LSVPEGAIAS LNCTY<u>SSWEG</u> <u>QS</u>FFWYRQYS

GKSPELIM<u>KL</u> YADPDKEDGR FTAQLNKASQ Y<u>V</u>SLLIRDS<u>Q</u>

<u>P</u>SDSATYLCA VRT<u>NSGYALN</u> FGKGTSLLVT P (b)
(SEQ ID NO: 3)
<u>A</u>KEVEQNSGP LSVPEGAIAS LNCTY<u>SSWEG</u> <u>QS</u>FFWYRQYS

GKSPELIM<u>F</u><u>L</u> YADPDKEDGR FTAQLNKASQ Y<u>V</u>SLLIRDS<u>Q</u>

<u>P</u>SDSATYLCA VRT<u>N</u><u>A</u>GYALN FGKGTSLLVT P
or (c)
(SEQ ID NO: 4)
<u>A</u>KEVEQNSGP LSVPEGAIAS LNCTY<u>SSWEG</u> <u>QS</u>FFWYRQYS

GKSPELIM<u>KL</u> YADPDKEDGR FTAQLNKASQ Y<u>V</u>SLLIRDS<u>Q</u>

<u>P</u>SDSATYLCA VRT<u>N</u><u>A</u>GYALN FGKGTSLLVT P, optionally with an N-terminal methionine (SEQ ID NOs: 41-43), and
the beta chain variable domain comprises the amino acid sequence:

(SEQ ID NO: 5)
DAGVTQSPTH LIKTRGQQVT LRCSPKSGHD TVSWYQQALG

QGPQFIFQAV RGVERQRGNF PDRFSGHQFP NYSSELNVNA

LLLGDSALYL CASSDTVSYE QYFGPGTRLT VT, optionally with an N-terminal methionine (SEQ ID NO: 44).
In the above amino acid sequences of the TCR alpha and TCR beta chain variable domains of the specific binding molecule of the invention, underlined residues represent the CDRs and double underlined residues represent mutations relative to the TCR alpha and TCR beta chain variable domains of a TCR disclosed in WO 2017163064 (referred to in FIGS. 1A and 1B herein respectively). Where amino acids are referred to herein by a numeric position, the numbering of that position assumes the presence of the optional N-terminal methionine.

In amino acid sequences SEQ ID NOs: 2, 3, and 4, CDR1 is SWEGQS (SEQ ID NO: 45), CDR2 is LYADPD (SEQ ID NO: 46), and CDR3 is CAVRTNAGYALNF (SEQ ID NO: 47).

The present invention provides specific binding molecules that can be produced with increased yields and/or that have unexpectedly high stability, while unexpectedly also retaining the favorable properties of the specific binding molecules from which they are derived. These include good antigen binding properties, including picomolar antigen affinity, a long binding half-life, the ability to mediate potent immune activation, when fused to an activating moiety, against HIV infected cells presenting extremely low levels of antigen, and a high level of specificity. The specific binding molecules of the invention are particularly suitable for use as soluble targeting reagents in treating HIV infected individuals.

The specific binding molecules or binding fragments thereof can be used to produce molecules with ideal therapeutic properties such as supra-physiological affinity for target, long binding half-life, high specificity for target and good stability. The invention also includes bispecific, or bifunctional, or fusion, molecules that incorporate specific binding molecules or binding fragments thereof and a T cell redirecting moiety. Such molecules can mediate a potent and specific response against HIV infected cells by redirecting and activating a polyclonal T-cell response. Furthermore, the use of specific binding molecules with supra-physiological affinity facilitates recognition and clearance of HIV-infected cells presenting low levels of peptide-HLA. Alternatively, the specific binding molecules or binding fragments may be fused to other therapeutic agents, and or diagnostic agents, and or incorporated in to engineered T cells for adoptive therapy.

The TCR domain sequences may be defined with reference to IMGT nomenclature which is widely known and accessible to those working in the TCR field. For example, see: LeFranc and LeFranc, (2001). "T cell Receptor Factsbook", Academic Press; Lefranc, (2011). Cold Spring Harb Protoc 2011(6): 595-603: Lefranc, (2001), Curr Protoc Immunol Appendix 1: Appendix 10; and Lefranc, (2003), Leukemia 17(1): 260-266. Briefly, αβ TCRs consist of two disulfide linked chains. Each chain (alpha and beta) is generally regarded as having two domains, namely a variable and a constant domain. A short joining region connects the variable and constant domains and is typically considered part of the alpha variable region. Additionally, the beta chain usually contains a short diversity region next to the joining region, which is also typically considered part of the beta variable region. The variable domain of each chain is located N-terminally and comprises three Complementarity Determining Regions (CDRs) embedded in a framework sequence (FR). The CDRs comprise the recognition site for peptide-MHC binding. There are several genes coding for alpha chain variable (Vα) regions and several genes coding for beta chain variable (Vβ) regions, which are distinguished by their framework, CDR1 and CDR2 sequences, and by a partly defined CDR3 sequence. The Vα and Vβ genes are referred to in IMGT nomenclature by the prefix TRAV and TRBV respectively (Folch and Lefranc, (2000), Exp Clin Immunogenet 17(1): 42-54: Scaviner and Lefranc, (2000), Exp Clin Immunogenet 17(2): 83-96; LeFranc and LeFranc, (2001), "T cell Receptor Factsbook", Academic Press). Likewise there are several joining or J genes, termed TRAJ or TRBJ, for the alpha and beta chain respectively, and for the beta chain, a diversity or D gene termed TRBD (Folch and Lefranc, (2000), Exp Clin Immunogenet 17(2): 107-114: Scaviner and Lefranc, (2000), Exp Clin Immunogenet 17(2): 97-106: LeFranc and LeFranc, (2001), "T cell Receptor Factsbook", Academic Press). The huge diversity of T cell receptor chains results from combinatorial rearrangements between the various V. J and D genes, which include allelic variants, and junctional diversity (Arstila, et al., (1999), Science 286(5441): 958-961: Robins et al., (2009), Blood 114(19): 4099-4107.) The constant, or C, regions of TCR alpha and beta chains are referred to as TRAC and TRBC respectively (Lefranc, (2001), Curr Protoc Immunol Appendix 1: Appendix 10).

As used herein, the term "specific binding molecule" refers to a molecule capable of binding specifically to a target antigen. Such molecules may adopt a number of different formats as discussed herein, and may be bispecific, i.e. they may have a first binding region that binds specifically to a first target antigen and a second binding region that binds specifically to a second target antigen. Furthermore, fragments of the specific binding molecules of the invention are also envisioned. A fragment refers to a portion of the specific binding molecule that retains specific binding to the target antigen.

The term 'mutations' encompasses substitutions, insertions and deletions. Mutations to a native (also referred to as parental, natural, unmutated, wild type, or scaffold) specific binding molecule may confer beneficial therapeutic properties, such as high affinity, high specificity and high potency; for example, mutations may that include those that increase the binding affinity ($k_D$) and/or binding half-life ($t_{1/2}$) of the specific binding molecule to the SLYNTVATL (SEQ ID NO: 1)-HLA-A*02 complex. In the present invention, mutations can additionally increase yield and/or stability, while unexpectedly retaining the above beneficial properties.

The alpha chain variable domain may comprise the amino acid sequence:

```
(a)
                                        (SEQ ID NO: 2)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNSGYALN FGKGTSLLVT P
```

The inventors have found that the mutation of the F residue at position 50 to K improves yield during production in *E. coli*, but unexpectedly without affecting target binding.

Alternatively, the alpha chain variable domain comprises the amino acid sequence:

```
b)
                                        (SEQ ID NO: 3)
AKEVEQNSGP LSVPEGAIAS LNCTYSSWEG QSFFWYRQYS

GKSPELIMFL YADPDKEDGR FTAQLNKASQ YVSLLIRDSQ

PSDSATYLCA VRTNAGYALN FGKGTSLLVT P
```

The inventors have found that the mutation of the S residue at position 96 to A improves stability, but again unexpectedly target binding is not affected.

Preferably, the alpha chain variable domain comprises the amino acid sequence:

```
c)
                                        (SEQ ID NO: 4)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNAGYALN FGKGTSLLVT P.
```

In the above amino acid sequences of the TCR alpha and TCR beta chain variable domains of the specific binding molecule of the invention, underlined residues represent the CDRs and double underlined residues represent mutations relative to the TCR alpha and TCR beta chain variable domains of a TCR disclosed in WO 2017163064 (referred to in FIGS. 1A and 1B herein respectively). Where amino acids are referred to herein by a numeric position, the numbering of that position assumes the presence of the optional N-terminal methionine.

In amino acid sequences SEQ ID NOs: 2, 3, and 4, CDR1 is SWEGQS (SEQ ID NO: 45), CDR2 is LYADPD (SEQ ID NO: 46), and CDR3 is CAVRTNAGYALNF (SEQ ID NO: 47).

A specific binding member comprising such an alpha chain variable domain unexpectedly has both improved yield and improved stability, with target binding being unaffected.

Specific binding molecules of the invention are amenable to high yield purification, particularly specific binding molecules in soluble format, and particularly when expressed in *E. coli*. Yield may be determined based on the amount of correctly folded material obtained at the end of the purification process relative to the original culture volume. Optionally yield is determined as in Example 1 herein. High yield typically means greater than 2 mg/L, or more preferably greater than 3 mg/L, or greater than 4 mg/L or greater than 5 mg/L, or higher yield.

Specific binding molecules of the invention may have improved stability, particularly in purified form. Stability in this context typically means the accumulation of breakdown products and or increase in heterogeneity of the purified material over time. Typically, accelerated stability studies may be performed to provide an indication of long term molecule stability: in such cases the purified material may be exposed to stress conditions, such as extreme temperatures or pH. For example, under conditions of high pH, the accumulation of acidic species may be used as a measure of molecule instability. This process is further described in Example 2 When measured under the conditions described in Example 2, the relative reduction in the main peak and corresponding increase in acidic species is preferably less than 35%, less than 30%, less than 25%, less than 20% and more preferably less than 15%. Additionally, or alternatively, stability may be assessed by measuring the relative abundance of amino acid modifications, such as deamidation, over time. Preferably, there is a change in relative abundance of less than 15%, less than 10%, less than 7%, less than 5%, less than 3% and more preferably less than 1%. Minimizing the risk of molecule instability is essential for successful clinical development.

In addition to the mutations discussed above, specific binding molecules of the invention may have one or more additional mutations in the alpha chain variable domain thereof. These mutations may be selected from A2Q, V73I, Q81K and P82L.

Combinations of these mutations may be as follows:
A2Q:
V73I:
Q81K:
P82L:
A2Q and V73I:
A2Q and Q81K:
A2Q and P82L:
V73I and Q81K:
V73I and P82L:
Q81K and P82L;
A2Q, V73I, and Q81K:
A2Q, V73I, and P82L;
V73I, Q81K, and P82L; or
A2Q, V73I, Q81K, and P82L.

These mutations may be made to any one of SEQ ID NOS: 41, 42, and 43.

Within the scope of the invention are phenotypically silent variants of any specific binding molecule of the invention disclosed herein. As used herein the term "phenotypically silent variants" is understood to refer to a specific binding molecule which incorporates one or more further amino acid changes, including substitutions, insertions and deletions, in addition to those set out above, which specific binding molecule has a similar phenotype to the corresponding specific binding molecule without said change(s). For the purposes of this application, specific binding molecule phenotype comprises antigen binding affinity ($K_D$ and/or binding half-life), antigen specificity, yield and stability. A phenotypically silent variant may have a $K_D$ and/or binding half-life for the SLYNTVATL (SEQ ID NO: 1) HLA-A*02 complex within 50%, or more preferably within 20%, of the measured $K_D$ and/or binding half-life of the corresponding specific binding molecule without said change(s), when measured under identical conditions (for example at 25° C. and on the same SPR chip). Suitable conditions are further provided in Example 3 in WO2017163064. Yield and stability are further defined above. Antigen specificity is further defined below. As is known to those skilled in the art, it may be possible to produce specific binding molecules that incorporate changes in the variable domains thereof compared to those detailed above without altering the affinity of the interaction with the SLYNTVATL (SEQ ID NO: 1) HLA-A*02 complex. In particular, such silent mutations may be incorporated within parts of the sequence that are known not to be directly involved in antigen binding (e.g. the framework regions, or parts of the CDRs that do not contact the peptide antigen). Such trivial variants are included in the scope of this invention.

Phenotypically silent variants may be produced by incorporating one or more conservative substitutions and/or one or more tolerated substitutions. By tolerated substitutions it is meant those substitutions which do not fall under the definition of conservative as provided below but are nonetheless phenotypically silent. By conservative substitutions it is meant the substitutions of one or more amino acids with alternative amino acids having sharing similar properties. The skilled person is aware that various amino acids have similar properties and thus are 'conservative'. One or more such amino acids of a protein, polypeptide or peptide can often be substituted by one or more other such amino acids without eliminating a desired activity of that protein, polypeptide or peptide. Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). It should be appreciated that amino acid substitutions within the scope of the present invention can be made using naturally occurring or non-naturally occurring amino acids. For example, it is contemplated herein that the methyl group on an alanine may be replaced with an ethyl group, and/or that minor changes may be made to the peptide backbone. Whether or not natural or synthetic amino acids are used, it is preferred that only L-amino acids are present.

Mutations, including conservative and tolerated substitutions, insertions and deletions, may be introduced into the sequences provided using any appropriate method including, but not limited to, those based on polymerase chain reaction (PCR), restriction enzyme-based cloning, or ligation independent cloning (LIC) procedures. These methods are detailed in many of the standard molecular biology texts. For further details regarding polymerase chain reaction (PCR) and restriction enzyme-based cloning, see Sambrook & Russell, (2001) Molecular Cloning—A Laboratory Manual ($3^{rd}$ Ed.) CSHL Press. Further information on ligation independent cloning (LIC) procedures can be found in Rashtchian. (1995) *Curr Opin Biotechnol* 6(1): 30-6. The specific binding molecule sequences provided by the invention may be obtained from solid state synthesis, or any other appropriate method known in the art.

The specific binding molecules of the invention have the property of binding the SLYNTVATL-HLA-A*02 complex ("SLYNTVATL" disclosed as SEQ ID NO: 1). Specific binding molecules of the invention demonstrate a high degree of specificity for SLYNTVATL-HLA-A*02 complex ("SLYNTVATL" disclosed as SEQ ID NO: 1) and are thus particularly suitable for therapeutic use. Specificity relates to the ability of the specific binding molecules of the invention to recognize target cells that are antigen positive, while having minimal ability to recognize target cells that are antigen negative. Antigen positive cells are those that have been determined to be infected with HIV and/or those that have been determined to present the SLYNTVATL-HLA-A*02 complex ("SLYNTVATL" disclosed as SEQ ID NO: 1), or escape variants of SLYNTVATL (SEQ ID NO: 1) presented by HLA-A*02 as discussed herein. The specific binding molecules of the invention may bind the complex of target peptide when bound to one of more HLA-A*02 subtypes, for example the specific binding molecules of the invention may bind the complex of the target peptide when bound to HLA-A*02:01 and/or the specific binding molecules of the invention may bind the complex of the target peptide when bound to HLA-A*02:05 and or HLA-A*02:06 and or HLA-A*02:07 and or HLA-A*02:02.

Specificity can be measured in vitro, for example, in cellular assays such as those described in Example 5 of WO2017163064. To test specificity, the specific binding molecules may be in soluble form and associated with an immune effector, and/or may be expressed on the surface of cells, such as T cells. Specificity may be determined by measuring the level of T cell activation in the presence of antigen positive and antigen negative target cells as defined above. Minimal recognition of antigen negative target cells is defined as a level of T cell activation of less than 20%, preferably less than 10%, preferably less than 5%, and more preferably less than 1%, of the level produced in the presence of antigen positive target cells, when measured under the same conditions and at a therapeutically relevant specific binding molecule concentration. For soluble TCRs associated with an immune effector, a therapeutically relevant concentration may be defined as a concentration of 10-9 M or below, and/or a concentration of up to 100, preferably up to 1000, fold greater than the corresponding EC50 or IC50 value. Preferably, for soluble specific binding molecules associated with an immune effector, there is at least a 100 fold, at least 1000 fold, at least 10000 fold difference in EC50 or IC50 value between T cell activation against antigen positive cells relative to antigen negative cells—this difference may be referred to as a therapeutic window. Additionally or alternatively the therapeutic window may be calculated based on lowest effective concentrations ("LOEL") observed for normal cells and the HIV-infected cells. Antigen positive cells may be obtained by peptide-pulsing using a suitable peptide concentration to obtain a low level of antigen presentation comparable to latently infected cells (for example, $10^{-9}$ M peptide, as described in Bossi et al., (2013) Oncoimmunol. 1:2 (11): e26840) or, they may naturally present said peptide. Preferably, both antigen positive and antigen negative cells are human cells. Preferably antigen positive cells are human cells, such as HIV infected CD4+ T cells. Antigen negative cells preferably include those derived from healthy human tissues, or non-HIV infected CD4+ T cells.

Specificity may additionally, or alternatively, relate to the ability of a specific binding molecule to bind to the SLYNTVATL-HLA-A*02 complex ("SLYNTVATL" disclosed as SEQ ID NO: 1) and not to a panel of alternative peptide-HLA complexes. Preferably, the alternative peptide-HLA complexes comprise HLA-A*02. This may, for example, be determined by the Biacore method of Example 3 of WO2017163064. Said panel may contain at least 5, and preferably at least 10, alternative peptide-HLA complexes. The alternative peptides may share a low level of sequence identity with SLYNTVATL (SEQ ID NO: 1) and may be naturally presented. Alternative peptides are preferably derived from proteins expressed in healthy human tissues (i.e. not cells infected with HIV). Binding of the specific binding molecule to the SLYNTVATL-HLA-A*02 complex ("SLYNTVATL" disclosed as SEQ ID NO: 1) may be at least 2 fold greater than to other naturally-presented peptide HLA complexes, more preferably at least 10 fold, or at least 100 fold or at least 1000 fold greater or at least 3000 fold greater.

An alternative or additional approach to determine specific binding molecule specificity may be to identify the peptide recognition motif of the specific binding molecule using sequential mutagenesis, e.g. alanine scanning, of the target peptide. Residues that form part of the binding motif are those that are not permissible to substitution. Non-permissible substitutions may be defined as those peptide positions in which the binding affinity of the specific binding molecule is reduced by at least 50%, or at least 80%, relative to the binding affinity for the non-mutated peptide. Such an approach is further described in Cameron et al., (2013), Sci Transl Med. 2013 Aug. 7: 5 (197): 197ra103 and WO2014096803 in connection with TCRs, though it will be appreciated that such methods can also be applied to the specific binding molecules of the present invention. Specific binding molecule specificity in this case may be determined by identifying alternative motif containing peptides, particularly alternative motif containing peptides in the human proteome, and testing these peptides for binding to the specific binding molecule. Binding of the specific binding molecule to one or more alternative peptides may indicate a lack of specificity. In this case further testing of specific binding molecule specificity via cellular assays may be required. A low tolerance for (alanine) substitutions in the central part of the peptide indicates that the specific binding molecule has a high specificity and therefore presents a low risk for cross-reactivity with alternative peptides.

Specific binding molecules of the invention may additionally bind to complexes containing natural escape variants of SLYNTVATL (SEQ ID NO: 1) presented by HLA-A*02. Escape variants of the peptide SLYNTVATL (SEQ ID NO: 1) have been isolated from AIDS patients and include the following (Sewell et al., (1997) Eur J Immunol. 27: 2323-2329):

| | |
|---|---|
| SLFNTVATL | (SEQ ID NO: 6) |
| SLFNTVAVL | (SEQ ID NO: 7) |
| SLSNTVATL | (SEQ ID NO: 8) |
| SSFNTVATL | (SEQ ID NO: 9) |
| SLLNTVATL | (SEQ ID NO: 10) |
| SLYNTIATL | (SEQ ID NO: 11) |
| SLYNTIAVL | (SEQ ID NO: 12) |
| SLFNTIATL | (SEQ ID NO: 13) |
| SLFNTIAVL | (SEQ ID NO: 14) |
| SLYNFVAVL | (SEQ ID NO: 15) |

Specific binding molecules of the invention may have an ideal safety profile for use as therapeutic reagents. In this case the specific binding molecules may be in soluble form and may preferably be fused to an immune effector. Suitable immune effectors include but are not limited to, cytokines, such as IL-2 and IFN-γ; superantigens and mutants thereof; chemokines such as IL-8, platelet factor 4, melanoma growth stimulatory protein; antibodies and antibody like scaffolds, including fragments, derivatives and variants thereof that bind to antigens on immune cells such as T cells or NK cell (e.g. anti-CD3, anti-CD28 or anti-CD16); and Fc receptor or complement activators. An ideal safety profile means that in addition to demonstrating good specificity, the specific binding molecules of the invention may have passed further preclinical safety tests. Examples of such tests include whole blood assays to confirm minimal cytokine release in the presence of whole blood and thus low risk of causing a potential cytokine release syndrome in vivo, and alloreactivity tests to confirm low potential for recognition of alternative HLA types.

Specific binding molecules of the invention preferably have a $K_D$ for the SLYNTVATL-HLA-A*02 complex ("SLYNTVATL" disclosed as SEQ ID NO: 1) of less than 100 nM, for example from about 50 nM to about 1 pM and/or have a binding half-life (T½) for the complex in the range of from about 1 min to about 50 h or more. Certain specific binding molecules of the invention may have a $K_D$ for the complex of from about 1 pM to about 1 nM, from about 1 pM to about 500 pM, from about 1 pM to about 300 pM. Certain TCRs of the invention may have a $K_D$ for the complex of about 50 pM to about 200 pM. Specific binding molecules of the invention may have a binding half-life ($T_{1/2}$) for the complex in the range of from about 1 min to about 50 h or more (such as 100 h), from about 30 min to about 50 h or more (such as 100 h), or from about 6 h to about 50 h or more (such as 100 h). All such specific binding molecules are highly suitable for use as therapeutics and/or diagnostics when coupled to a detectable label or therapeutic agent. Certain specific binding molecules of the invention may be suitable for adoptive therapy applications, such specific binding molecules may have a $K_D$ for the complex of from about 50 nM to about 200 nM, and/or a binding half-life for the complex of from about 3s sec to about 12 min.

Methods to determine binding affinity (inversely proportional to the equilibrium constant $K_D$) and binding half life (expressed as T½) are known to those skilled in the art. In a preferred embodiment, binding affinity and binding half-life are determined using Surface Plasmon Resonance (SPR) or Bio-Layer Interferometry (BLI), for example using a BIAcore instrument or Octet instrument, respectively. A preferred method is provided in Example 3 of WO2017163064. It will be appreciated that doubling the affinity of a specific binding molecule results in halving the $K_D$. T½ is calculated as In2 divided by the off-rate ($k_{off}$). Therefore, doubling of T½ results in a halving in $k_{off}$. $K_D$ and $k_{off}$ values for TCRs are usually measured for soluble forms of the TCR, i.e. those forms which are truncated to remove cytoplasmic and transmembrane domain residues (including single chain TCRs and or TCR incorporating a non-native disulfide bond or other dimerization domain). To account for variation between independent measurements, and particularly for interactions with dissociation times in excess of 20 hours, the binding affinity and or binding half-life of a given specific binding molecule may be measured several times, for example 3 or more times, using the same assay protocol, and an average of the results taken. To compare binding data between two samples (i.e. two different specific binding molecules and or two preparations of the same specific binding molecule) it is preferable that measurements are made using the same assay conditions (e.g. temperature), such as those described in Example 3 of WO2017163064.

Certain preferred mutated specific binding molecules of the invention are able to generate a highly potent T cell response in vitro against antigen positive cells, in particular those cells presenting low levels of antigen (i.e. in the order of 5-100) typical of HIV infected CD4 cells. Such specific binding molecules may be in soluble form and linked to an immune effector such as an anti-CD3 antibody. The T cell response that is measured may be the release of T cell activation markers such as Interferon γ or Granzyme B, or target cell killing, or other measure of T cell activation, such as T cell proliferation. Preferably a highly potent response is one with EC50 or IC50 value in the pM range, for example, 100 pM or lower, preferably 50 pM or lower, for example between 50 pM and 1 pM.

Specific binding molecules of the invention may comprise TCR variable domains. Preferably the TCR variable domains comprise a heterodimer of alpha and beta chains. In the specific binding molecules of the invention the variable domains and where present the constant domains, and or any other domains, may be organised in any suitable format/arrangement. Examples of such arrangements are well known in the antibody art. The skilled person is aware of the similarities between antibodies and TCRs and could apply such arrangements to TCR variable and constant domains (Brinkman et al., MAbs. 2017 February-March: 9(2): 182-212). For example, the variable domains may be arranged in monoclonal TCR format, in which the two chains are linked by a disulfide bond, either within the constant domains or variable domains, or in which the variable domains are fused to one or more dimerization domains. Alternatively the variable domains may be arranged in single chain format in the present or absence of one or more constant domains, or the variable domains may be arranged in diabody format.

Specific binding molecules of the invention may comprise at least one TCR constant domain or fragment thereof, for example an alpha chain TRAC constant domain and/or a beta chain TRBC1 or TRBC2 constant domain. As will be appreciated by those skilled in the art the term TRAC and TRBC1/2 also encompasses natural polymorphic variants, for example N to K at position 4 of TRAC (Bragado et al International immunology. 1994 February:6(2):223-30).

Where present, one or both of the constant domains may contain mutations, substitutions or deletions relative to native constant domain sequences. The constant domains may be truncated, i.e. having no transmembrane or cytoplasmic domains. Alternatively the constant domains may be full-length by which it is meant that extracellular, transmembrane and cytoplasmic domains are all present. The TRAC and TRBC domain sequences may be modified by truncation or substitution to delete the native disulfide bond between Cys4 of exon 2 of TRAC and Cys2 of exon 2 of TRBC1 or TRBC2. The alpha and/or beta chain constant domain sequence(s) may have an introduced disulfide bond between residues of the respective constant domains, as described, for example, in WO 03/020763. Preferably the alpha and beta constant domains may be modified by substitution of cysteine residues at position Thr 48 of TRAC and position Ser 57 of TRBC1 or TRBC2, the said cysteines forming a non-natural disulfide bond between the TCR alpha and beta constant domains. TRBC1 or TRBC2 may additionally include a cysteine to alanine mutation at position 75 of the constant domain and an asparagine to aspartic acid mutation at position 89 of the constant domain. One or both of the extracellular constant domains present in an αβ heterodimer of the invention may be further truncated at the C terminus or C termini, for example by up to 15, or up to 10, or up to 8 or fewer amino acids. One or both of the extracellular constant domains present in an αβ heterodimer of the invention may be truncated at the C terminus or C termini by, for example, up to 15, or up to 10 or up to 8 amino acids. The C terminus of the alpha chain extracellular constant domain may be truncated by 8 amino acids.

Alternatively, rather than full-length or truncated constant domains there may be no TCR constant domains. Accordingly, the specific binding molecule of the invention may be comprised of the variable domains of the TCR alpha and beta chains, optionally with additional domains as described herein. Additional domains include but are not limited to immune effector domains (such as antibody domains), Fc domains or albumin binding domains, therapeutic agents or detectable labels.

Single chain formats include, but are not limited to, αβ TCR polypeptides of the Vα-L-Vβ, Vβ-L-Vα, Vα-Cα-L-Vβ, Vα-L-Vβ-Cβ, or Vα-Cα-L-Vβ-Cβ types, wherein Vα and Vβ are TCR α and β variable regions respectively, Cα and Cβ are TCR α and β constant regions respectively, and L is a linker sequence (Weidanz et al., (1998) J Immunol Methods. December 1;221(1-2):59-76; Epel et al., (2002), Cancer Immunol Immunother. November:51(10):565-73: WO 2004/033685: WO9918129). Linker sequences are usually flexible, in that they are made up primarily of amino acids such as glycine, alanine and serine, which do not have bulky side chains likely to restrict flexibility. Alternatively, linkers with greater rigidity may be desirable. Usable or optimum lengths of linker sequences may be easily determined. Often the linker sequence will be less than about 12, such as less than 10, or from 2-10 amino acids in length, The linker may be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids in length. Examples of suitable linkers that may be used multi-domain binding molecules of the invention include, but are not limited to: GGGGS (SEQ ID NO: 16), GGGSG (SEQ ID NO: 17), GGSGG (SEQ ID NO: 18), GSGGG (SEQ ID NO: 19), GSGGGP (SEQ ID NO: 20), GGEPS (SEQ ID NO: 21), GGEGGGP (SEQ ID NO: 22), and GGEGGGSEGGGS (SEQ ID NO: 23) (as described in WO2010/133828) and GGGSGGGG (SEQ ID NO: 24). Additional linkers may include sequences having one or more of the following sequence motifs: GGGS (SEQ ID NO: 25), GGGGS (SEQ ID NO: 26), TVLRT (SEQ ID NO: 27), TVSSAS (SEQ ID NO: 28) and TVLSSAS (SEQ ID NO: 29). Where present, one or both of the constant domains may be full length, or they may be truncated and/or contain mutations as described above. Preferably single chain TCRs are soluble. In certain embodiments single chain TCRs of the invention may have an introduced disulfide bond between residues of the respective constant domains, as described in WO 2004/033685. Single chain TCRs are further described in WO2004/033685; WO98/39482; WO01/62908; Weidanz et al. (1998) J Immunol Methods 221(1-2); 59-76; Hoo et al. (1992) Proc Natl Acad Sci USA 89(10): 4759-4763; Schodin (1996) Mol Immunol 33(9): 819-829).

The TCR variable domains may be arranged in diabody format. In the diabody format two single chain fragments dimerize in a head-to-tail orientation resulting in a compact molecule with a molecular mass similar to tandem scFv (~50 kDa).

The invention also includes particles displaying specific binding molecules of the invention and the inclusion of said particles within a library of particles. Such particles include but are not limited to phage, yeast cells, ribosomes, or mammalian cells. Method of producing such particles and libraries are known in the art (for example see WO2004/044004: WO01/48145, Chervin et al. (2008) J. Immuno. Methods 339.2: 175-184).

Specific binding molecules of the invention are useful for delivering detectable labels or therapeutic agents to antigen presenting cells and tissues containing antigen presenting cells. They may therefore be associated (covalently or otherwise) with a detectable label (for diagnostic purposes wherein the specific binding molecule is used for example to detect the presence of cells presenting the cognate antigen); and or a therapeutic agent, including immune effectors; and or a pharmacokinetic (PK) modifying moiety.

Examples of PK modifying moieties include, but are not limited to, PEG (Dozier et al., (2015) Int J Mol Sci. October 28;16(10):25831-64 and Jevsevar et al., (2010) Biotechnol J. January;5(1): 113-28), PASylation (Schlapschy et al., (2013) Protein Eng Des Sel. August;26(8):489-501), albumin, and albumin binding domains, (Dennis et al., (2002) J Biol Chem. September 20;277(38):35035-43), and/or unstructured polypeptides (Schellenberger et al., (2009) Nat Biotechnol. December;27(12): 1186-90). Further PK modifying moieties include antibody Fc fragments. PK modifying moieties may serve to extend the in vivo half-life of specific binding molecules of the invention.

Where an immunoglobulin Fc domain is used, it may be any antibody Fc region. The Fc region is the tail region of an antibody that interacts with cell surface Fc receptors and some proteins of the complement system. The Fc region typically comprises two polypeptide chains both having two or three heavy chain constant domains (termed CH2, CH3 and CH4), and a hinge region. The two chains being linked by disulfide bonds within the hinge region. Fc domains from immunoglobulin subclasses IgG1, IgG2 and IgG4 bind to and undergo FcRn mediated recycling, affording a long circulatory half-life (3-4 weeks). The interaction of IgG with FcRn has been localized in the Fc region covering parts of the CH2 and CH3 domain. Preferred immunoglobulin Fc for use in the present invention include, but are not limited to, Fc domains from IgG1 or IgG4. Preferably the Fc domain is derived from human sequences. The Fc region may also preferably include KiH mutations which facilitate dimerization, as well as mutations to prevent interaction with activating receptors i.e. functionally silent molecules. The immunoglobulin Fc domain may be fused to the C or N terminus of the other domains (i.e., the TCR variable domains and/or TCR constant domains and/or immune effector domains), in any suitable order or configuration. The immunoglobulin Fc may be fused to one or more of the other domains (i.e., the TCR variable domains and/or TCR constant domains and/or an immune effector domains) via a linker. Linker sequences are usually flexible, in that they are made up primarily of amino acids such as glycine, alanine and serine, which do not have bulky side chains likely to restrict flexibility. Alternatively, linkers with greater rigidity may be desirable. Usable or optimum lengths of linker sequences may be easily determined. Often the linker sequence will be less than about 12, such as less than 10, or from 2-10 amino acids in length. The linker may be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids in length Examples of suitable linkers that may be used multi-domain binding molecules of the invention include, but are not limited to: GGGGS (SEQ ID NO: 16), GGGSG (SEQ ID NO: 17), GGSGG (SEQ ID NO: 18), GSGGG (SEQ ID NO: 19), GSGGGP (SEQ ID NO: 20), GGEPS (SEQ ID NO: 21), GGEGGGP (SEQ ID NO: 22), and GGEGGGSEGGGS (SEQ ID NO: 23) (as described in WO2010/133828) and GGGSGGGG (SEQ ID NO: 24). Additional linkers may include sequences having one or more of the following sequence motifs: GGGS (SEQ ID NO: 25), GGGGS (SEQ ID NO: 26), TVLRT (SEQ ID NO: 27), TVSSAS (SEQ ID NO: 28) and TVLSSAS (SEQ ID NO: 29). Where the immunoglobulin Fc is fused to the TCR, it may be fused to either the alpha or beta chains, with or without a linker. Furthermore, individual chains of the Fc may be fused to individual chains of the TCR.

Preferably the Fc region may be derived from the IgG1 or IgG4 subclass. The two chains may comprise CH2 and CH3 constant domains and all or part of a hinge region. The hinge region may correspond substantially or partially to a hinge region from IgG1, IgG2, IgG3 or IgG4. The hinge may comprise all or part of a core hinge domain and all or part of a lower hinge region. Preferably, the hinge region contains at least one disulfide bond linking the two chains.

The Fc region may comprise mutations relative to a WT sequence. Mutations include substitutions, insertions and deletions. Such mutations may be made for the purpose of introducing desirable therapeutic properties. For example, to facilitate heterodimerzation, knobs into holes (KiH) mutations may be engineered into the CH3 domain. In this case, one chain is engineered to contain a bulky protruding residue (i.e. the knob), such as Y, and the other is chain engineered to contain a complementary pocket (i.e. the hole). Suitable positions for KiH mutations are known in the art. Additionally or alternatively mutations may be introduced that abrogate or reduce binding to Fcγ receptors and or increase binding to FcRn, and/or prevent Fab arm exchange, or remove protease sites. Additionally or alternatively, mutations may be made to improve manufacturability for example to remove or alter glycosylation sites.

The PK modifying moiety may also be an albumin-binding domain, which may also act to extend half-life. As is known in the art, albumin has a long circulatory half-life of 19 days, due in part to its size, being above the renal threshold, and by its specific interaction and recycling via FcRn. Attachment to albumin is a well-known strategy to improve the circulatory half-life of a therapeutic molecule in vivo. Albumin may be attached non-covalently, through the use of a specific albumin binding domain, or covalently, by conjugation or direct genetic fusion. Examples of therapeutic molecules that have exploited attachment to albumin for improved half-life are given in Sleep et al., Biochim Biophys Acta. 2013 December: 1830(12):5526-34.

The albumin-binding domain may be any moiety capable of binding to albumin, including any known albumin-binding moiety. Albumin binding domains may be selected from endogenous or exogenous ligands, small organic molecules, fatty acids, peptides and proteins that specifically bind albumin. Examples of preferred albumin binding domains include short peptides, such as described in Dennis et al., J Biol Chem. 2002 Sep. 20:277(38):35035-43 (for example the peptide QRLMEDICLPRWGCLWEDDF (SEQ ID NO: 37)); proteins engineered to bind albumin such as antibodies, antibody fragments and antibody like scaffolds, for example Albudab® (O'Connor-Semmes et al., Clin Pharmacol Ther. 2014 December:96(6): 704-12), commercially provided by GSK and Nanobody R; (Van Roy et al., Arthritis Res Ther. 2015 May 20:17:135), commercially provided by Ablynx; and proteins based on albumin binding domains found in nature such as Streptococcal protein G Protein (Stork et al., Eng Des Sel. 2007 November:20(11):569-76), for example Albumod® commercially provided by Affibody.

Preferably, albumin is human serum albumin (HSA). The affinity of the albumin binding domain for human albumin may be in the range of picomolar to micromolar. Given the extremely high concentration of albumin in human serum (35-50 mg/ml, approximately 0.6 mM), it is calculated that substantially all of the albumin binding domains will be bound to albumin in vivo.

The albumin-binding moiety may be fused to the C or N terminus of the other domains (i.e., the TCR variable domains and/or TCR constant domains and/or immune effector domains), in any suitable order or configuration. The albumin-binding moiety may be fused to one or more of the other domains (i.e., the TCR variable domains and/or TCR constant domains and/or an immune effector domains) via a linker. Linker sequences are usually flexible, in that they are made up primarily of amino acids such as glycine, alanine and serine, which do not have bulky side chains likely to restrict flexibility. Alternatively, linkers with greater rigidity may be desirable. Usable or optimum lengths of linker sequences may be easily determined. Often the linker sequence will be less than about 12, such as less than 10, or from 2-10 amino acids in length. The liker may be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids in length. Examples of suitable linkers that may be used multi-domain binding molecules of the invention include, but are not limited to: GGGGS (SEQ ID NO: 16), GGGSG (SEQ ID NO: 17), GGSGG (SEQ ID NO: 18), GSGGG (SEQ ID NO: 19), GSGGGP (SEQ ID NO: 20), GGEPS (SEQ ID NO: 21), GGEGGGP (SEQ ID NO: 22), and GGEGGGSEGGGS (SEQ ID NO: 23) (as described in WO2010/133828) and GGGSGGGG (SEQ ID NO: 24). Additional linkers may include sequences having one or more of the following sequence motifs: GGGS (SEQ ID NO: 25), GGGGS (SEQ ID NO: 26), TVLRT (SEQ ID NO: 27), TVSSAS (SEQ ID NO: 28) and TVLSSAS (SEQ ID NO: 29). Where the albumin-binding moiety is linked to the specific binding molecule, it may be linked to either the alpha or beta chains, with or without a linker.

Detectable labels for diagnostic purposes include for instance, fluorescent labels, radiolabels, enzymes, nucleic acid probes and contrast reagents.

For some purposes, the specific binding molecules of the invention may be aggregated into a complex comprising several specific binding molecules to form a multivalent specific binding molecule complex. There are a number of human proteins that contain a multimerisation domain that may be used in the production of multivalent specific binding molecule complexes. For example the tetramerisation domain of p53 which has been utilised to produce tetramers of scFv antibody fragments which exhibited increased serum persistence and significantly reduced off-rate compared to the monomeric scFv fragment (Willuda et al. (2001) J. Biol. Chem. 276 (17) 14385-14392). Haemoglobin also has a tetramerisation domain that could be used for this kind of application. A multivalent specific binding molecule complex of the invention may have enhanced binding capability for the complex compared to a non-multimeric native (also referred to as parental, natural, unmutated wild type, or scaffold) T cell receptor heterodimer of the invention. Thus, multivalent complexes of specific binding molecules of the invention are also included within the invention. Such multivalent specific binding molecule complexes according to the invention are particularly useful for tracking or targeting cells presenting particular antigens in vitro or in vivo, and are also useful as intermediates for the production of further multivalent specific binding molecule complexes having such uses.

Therapeutic agents which may be associated with the specific binding molecules of the invention include immune-modulators and effectors, radioactive compounds, enzymes (perforin for example) or chemotherapeutic agents (cisplatin for example). To ensure that the therapeutic effects are exercised in the desired location the agent could be inside a liposome or other nanoparticle structure linked to the specific binding molecule so that the compound is released slowly. This will prevent damaging effects during the transport in the body and ensure that the agent has maximum effect after binding of the specific binding molecule to the relevant antigen presenting cells.

Examples of suitable therapeutic agents include, but are not limited to:
- antibodies, or fragments thereof, including anti-T cell or NK cell determinant antibodies (e.g. anti-CD3, anti-CD28 or anti-CD16)
- alternative protein scaffolds with antibody-like binding characteristics (e.g. DARPins)
- immuno-stimulants, i.e. immune effector molecules which stimulate immune response. For example, cytokines such as IL-2 and IFN-γ,
- chemokines such as IL-8, platelet factor 4, melanoma growth stimulatory protein, etc.
- activators of the complement pathway or Fc receptors
- checkpoint inhibitors, such as those that target PD1 or PD-L1
- small molecule cytotoxic agents, i.e. compounds with the ability to kill mammalian cells having a molecular weight of less than 700 Daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate arbourate, auristatin E vincristine and doxorubicin peptide cytotoxins, i.e. proteins or fragments thereof with the ability to kill mammalian cells. For example, ricin, diphtheria toxin, *pseudomonas* bacterial exotoxin A, Dnase and Rnase:

radio-nuclides, i.e. unstable isotopes of elements which decay with the concurrent emission of one or more of α or β particles, or γ rays. For example, iodine 131, rhenium 186, indium 111, yttrium 90, bismuth 210 and 213, actinium 225 and astatine 213: chelating agents may be used to facilitate the association of these radio-nuclides to TCRs, or multimers thereof:

superantigens and mutants thereof peptide-HLA complex, wherein said peptide is derived from a common human pathogen, such as Epstein Barr Virus (EBV)

xenogeneic protein domains, allogeneic protein domains, viral/bacterial protein domains, viral/bacterial peptides Preferred is a soluble specific binding molecule of the invention associated (usually by fusion to the N- or C-terminus of the alpha or beta chain, or both, in any suitable configuration) with an immune effector. The N terminus of the TCR may be linked to the C-terminus of the immune effector polypeptide.

A particularly preferred immune effector is an anti-CD3 antibody, or a functional fragment or variant of said anti-CD3 antibody. Specific binding molecules of the invention comprising such an antibody are bispecific and may be referred to herein as "fusion molecules". As used herein, the term "antibody" encompasses such fragments and variants. Examples of anti-CD3 antibodies include but are not limited to OKT3, UCHT-1, BMA-031 and 12F6. Antibody fragments and variants/analogues which are suitable for use in the compositions and methods described herein include minibodies, diabodies, Fab fragments, F(ab')₂ fragments, dsFv and scFv fragments. Further examples encompassed within the term antibodies include Nanobodies™ (these constructs, marketed by Ablynx (Belgium), comprising synthetic single immunoglobulin variable heavy domain derived from a camelid (e.g. camel or llama) antibody), Domain Antibodies (Domantis, Belgium), comprising an affinity matured single immunoglobulin variable heavy domain or immunoglobulin variable light domain, and alternative protein scaffolds that exhibit antibody like binding characteristics, such as Affibodies (Affibody, Sweden), comprising engineered protein A scaffold, or Anticalins (*Pieris*, Germany), comprising engineered anticalins, or DARPins (Molecular Partners, Switzerland), comprising designed ankyrin repeat proteins.

The anti-CD3 antibody may be covalently linked to the C- or N-terminus of the TCR alpha or beta chain. The anti-CD3 antibody may be covalently linked to the C- or N-terminus of the TCR beta chain of the TCR via a linker sequence.

Preferably the anti-CD3 is an scFV fragment. Alternatively, the heavy and light variable domain fragments may be arranged in a diabody orientation. Particularly preferred anti-CD3 sequences are provided in WO2020157210 and WO2017163064.

Examples of preferred arrangements of fusion molecules include those described in WO2010133828, WO2020157211 WO2019012138 and WO2019012141. The format described in WO2010133828 is particularly preferred.

The specific binding molecule of the invention may comprise:
a first polypeptide chain which comprises the alpha chain variable domain and a first binding region of a variable domain of an antibody; and
a second polypeptide chain which comprises the beta chain variable domain and a second binding region of a variable domain of said antibody,
wherein the respective polypeptide chains associate such that the specific binding molecule is capable of simultaneously binding SLYNTVATL-HLA-A2 complex ("SLYNTVATL" disclosed as SEQ ID NO: 1) and an antigen of the antibody.

There is also provided herein a dual specificity polypeptide molecule selected from the group of molecules comprising a first polypeptide chain and a second polypeptide chain, wherein: the first polypeptide chain comprises a first binding region of a variable domain (VD1) of an antibody specifically binding to a cell surface antigen of a human immune effector cell, and
a first binding region of a variable domain (VR1) of a TCR specifically binding to an MHC-associated peptide epitope, and
a first linker (LINK1) connecting said domains:
the second polypeptide chain comprises a second binding region of a variable domain (VR2) of a TCR specifically binding to an MHC-associated peptide epitope, and
a second binding region of a variable domain (VD2) of an antibody specifically binding to a cell surface antigen of a human immune effector cell, and
a second linker (LINK2) connecting said domains:
wherein said first binding region (VD1) and said second binding region (VD2) associate to form a first binding site (VD1)(VD2) that binds a cell surface antigen of a human immune effector cell:
said first binding region (VR1) and said second binding region (VR2) associate to form a second binding site (VR1)(VR2) that binds said MHC-associated peptide epitope:
wherein said two polypeptide chains are fused to human IgG hinge domains and/or human IgG Fc domains or dimerizing portions thereof; and
wherein the said two polypeptide chains are connected by covalent and/or non-covalent bonds between said hinge domains and/or Fc-domains; and
wherein said dual specificity polypeptide molecule is capable of simultaneously binding the cell surface molecule and the MHC-associated peptide epitope, and dual specificity polypeptide molecules, wherein the order of the binding regions in the two polypeptide chains is selected from VD1-VR1 and VR2-VD2 or VD1-VR2 and VR1-VD2, or VD2-VR1 and VR2-VD1 or VD2-VR2 and VR1-VD1 and wherein the domains are either connected by LINK1 or LINK2, wherein the MHC-associated peptide epitope is SLYNTVATL (SEQ ID NO: 1) complex and the MHC is HLA-A*02.

Linkage of the specific binding molecule and the anti-CD3 antibody may be via covalent or non-covalent attachment. Covalent attachment may be direct, or indirect via a linker sequence. Linker sequences are usually flexible, in that they are made up primarily of amino acids such as glycine, alanine and serine, which do not have bulky side chains likely to restrict flexibility. Alternatively, linkers with greater rigidity may be desirable. Usable or optimum lengths of linker sequences may be easily determined. Often the linker sequence will be less than about 12, such as less than 10, or from 2-10 amino acids in length. Examples of suitable linkers that may be used multi-domain binding molecules of the invention include, but are not limited to: GGGGS (SEQ ID NO: 16), GGGSG (SEQ ID NO: 17), GGSGG (SEQ ID NO: 18), GSGGG (SEQ ID NO: 19), GSGGGP (SEQ ID NO: 20), GGEPS (SEQ ID NO: 21), GGEGGGP (SEQ ID NO: 22), and GGEGGGSEGGGS (SEQ ID NO: 23) (as described in WO2010/133828) and GGGSGGGG (SEQ ID NO: 24). Additional linkers may include sequences having one or more of the following sequence motifs: GGGS (SEQ ID NO: 25), GGGGS (SEQ ID NO: 26), TVLRT (SEQ ID NO: 27), TVSSAS (SEQ ID NO: 28) and TVLSSAS (SEQ ID NO: 29).

A preferred specific binding molecule of the invention has a beta chain comprising the amino acid sequence:

```
                                              (SEQ ID NO: 30)
AIQMTQSPS SLSASVGDRV TITCRASQDI RNYLNWYQQK

PGKAPKLLIY YTSRLESGVP SRFSGSGSGT DYTLTISSLQ

PEDFATYYCQ QGNTLPWTFG QGTKVEIKGG GGSGGGGSGG

GGSGGGGSGG GSEVQLVESG GGLVQPGGSL RLSCAASGYS

FTGYAMNWVR QAPGKGLEWV ALINPYKGVS TYNQKFKDRF

TFSVDKSKNT AYLQMNSLRA EDTAVYYCAR SGYYGDSDWY

FDVWGQGTLV TVSSGGGGSD AGVTQSPTHL IKTRGQQVTL

RCSPKSGHDT VSWYQQALGQ GPQFIFQAVR GVERQRGNFP

DRFSGHQFPN YSSELNVNAL LLGDSALYLC ASSDTVSYEQ

YFGPGTRLTV TEDLKNVFPP EVAVFEPSEA EISHTQKATL

VCLATGFYPD HVELSWWVNG KEVHSGVCTD PQPLKEQPAL

NDSRYALSSR LRVSATFWQD PRNHFRCQVQ FYGLSENDEW

TQDRAKPVTQ IVSAEAWGRA D
```

An alternative specific binding molecule of the invention has a beta chain comprising the amino acid sequence:

```
                                              (SEQ ID NO: 31)
AIQMTQSPS SLSASVGDRV TITCRASQDI RNYLNWYQQK

PGKAPKLLIY YTSRLESGVP SRFSGSGSGT DYTLTISSLQ

PEDFATYYCQ QGNTLPWTFG QGTKVEIKGG GGSGGGGSGG

GGSGGGGSGG GSEVQLVESG GGLVQPGGSL RLSCAASGYS

FTGYTMNWVR QAPGKGLEWV ALINPYKGVS TYNQKFKDRF

TISVDKSKNT AYLQMNSLRA EDTAVYYCAR SGYYGDSDWY

FDVWGQGTLV TVSSGGGGSD AGVTQSPTHL IKTRGQQVTL

RCSPKSGHDT VSWYQQALGQ GPQFIFQAVR GVERQRGNFP

DRFSGHQFPN YSSELNVNAL LLGDSALYLC ASSDTVSYEQ

YFGPGTRLTV TEDLKNVFPP EVAVFEPSEA EISHTQKATL

VCLATGFYPD HVELSWWVNG KEVHSGVCTD PQPLKEQPAL
```

-continued
```
NDSRYALSSR LRVSATFWQD PRNHFRCQVQ FYGLSENDEW

TQDRAKPVTQ IVSAEAWGRA D
```

A preferred alpha chain comprises the amino acid sequence:

```
                                              (SEQ ID NO: 32)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNAGYALN FGKGTSLLVT PHIQKPDPAV

YQLRDSKSSD KSVCLFTDFD SQTNVSQSKD SDVYITDKCV

LDMRSMDFKS NSAVAWSNKS DFACANAFNN SIIPEDT
```

In the above amino acid sequences of the specific binding molecule of the invention, underlined residues represent the CDRs. In amino acid sequences SEQ ID NO: 30 and 31, CDR1 is SGHDT (SEQ ID NO: 48), CDR2 is AVRGVE (SEQ ID NO: 49), and CDR3 is CASSDTVSYEQYF (SEQ ID NO: 50).

A preferred specific binding molecule of the present invention comprises the amino acid sequences of SEQ ID NOS: 30 and 32.

Also included within the scope of the invention are functional variants (also known as phenotypically silent variants) of said specific binding molecules comprising an anti-CD3.

In a further aspect, the present invention provides nucleic acid encoding a TCR alpha chain and/or a TCR beta chain of the invention. Also provided is nucleic acid encoding a specific binding molecule of the invention, including such molecules fused to an anti-CD3 antibody or fragment thereof. In some embodiments, the nucleic acid is cDNA. In some embodiments the nucleic acid may be mRNA, for example, mRNA encoded bispecific molecules (Stadler et al., Nat Med. 2017 July:23(7):815-817). In some embodiments, the invention provides nucleic acid comprising a sequence encoding a TCR α chain variable domain of a specific binding molecule of the invention. In some embodiments, the invention provides nucleic acid comprising a sequence encoding a TCR β chain variable domain of a specific binding molecule of the invention. The nucleic acid may be non-naturally occurring and/or purified and/or engineered. The nucleic acid sequence may be codon optimised, in accordance with expression system utilised. As is known to those skilled in the art, expression systems may include bacterial cells such as *E. coli*, or yeast cells, or mammalian cells, or insect cells, or they may be cell free expression systems. In some embodiments the molecules may be mRNA encoded bispecific antibodies.

In another aspect, the invention provides a vector which comprises nucleic acid of the invention. Preferably the vector is a TCR expression vector. Suitable TCR expression vectors include, for example, gamma-retroviral vectors or, more preferably, lentiviral vectors. Further details can be found in Zhang 2012 and references therein (Zhang et al., Adv Drug Deliv Rev. 2012 Jun. 1: 64(8): 756-762).

The invention also provides a cell harbouring a vector of the invention, preferably a TCR expression vector. Suitable cells include, mammalian cells, preferably immune cells, even more preferably T cells. The vector may comprise nucleic acid of the invention encoding in a single open reading frame, or two distinct open reading frames, encoding the alpha chain and the beta chain respectively. Another aspect provides a cell harbouring a first expression vector which comprises nucleic acid encoding the alpha chain of a specific binding molecule of the invention, and a second expression vector which comprises nucleic acid encoding the beta chain of a specific binding molecule of the invention. Such cells are particularly useful in adoptive therapy. The cells of the invention may be isolated and/or recombinant and/or non-naturally occurring and/or engineered.

Since the specific binding molecules of the invention have utility in adoptive therapy, the invention includes a non-naturally occurring and/or purified and/or or engineered cell, especially a T-cell, presenting a specific binding molecule of the invention. The invention also provides an expanded population of T cells presenting a specific binding molecule of the invention. There are a number of methods suitable for the transfection of T cells with nucleic acid (such as DNA, cDNA or RNA) encoding the specific binding molecules of the invention (see for example Robbins et al., (2008) J Immunol. 180): 6116-6131). T cells expressing the specific binding molecules of the invention will be suitable for use in adoptive therapy-based treatment of cancer. As will be known to those skilled in the art, there are a number of suitable methods by which adoptive therapy can be carried out (see for example Rosenberg et al., (2008) Nat Rev Cancer 8(4)).

As is well-known in the art, in vivo production of proteins including those comprising the specific binding molecules of the invention may result in post translational modifications. Glycosylation is one such modification, which comprises the covalent attachment of oligosaccharide moieties to defined amino acids in the polypeptide chain. For example, asparagine residues, or serine/threonine residues are well-known locations for oligosaccharide attachment. The glycosylation status of a particular protein depends on a number of factors, including protein sequence, protein conformation and the availability of certain enzymes. Furthermore, glycosylation status (i.e. oligosaccharide type, covalent linkage and total number of attachments) can influence protein function. Therefore, when producing recombinant proteins, controlling glycosylation is often desirable. Controlled glycosylation has been used to improve antibody based therapeutics. (Jefferis et al., (2009) Nat Rev Drug Discov March: 8(3):226-34). For the specific binding molecules of the invention glycosylation may be controlled, by using particular cell lines for example (including but not limited to mammalian cell lines such as Chinese hamster ovary (CHO) cells or human embryonic kidney (HEK) cells), or by chemical modification. Such modifications may be desirable, since glycosylation can improve pharmacokinetics, reduce immunogenicity and more closely mimic a native human protein (Sinclair and Elliott, (2005) Pharm Sci. August: 94(8): 1626-35). In some cases, mutations may be introduced to control and or modify post translational modifications.

For administration to patients, the specific binding molecules of the invention (preferably associated with a detectable label or therapeutic agent such as anti-CD3 or expressed on a transfected T cell), nucleic acids, expression vectors or cells of the invention may be provided as part of a sterile pharmaceutical composition together with one or more pharmaceutically acceptable carriers or excipients. This pharmaceutical composition may be in any suitable form. (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, such as parenteral (including subcutaneous, intramuscular, intrathecal or intravenous), enteral (including oral or rectal), inhalation or intranasal routes. Such compositions may be prepared by any method known in the art of pharmacy, for example by mixing the active ingredient with the carrier(s) or excipient (s) under sterile conditions.

Dosages of the substances of the present invention can vary between wide limits, depending upon the disease or disorder to be treated, the age and condition of the individual to be treated, etc. a suitable dose range for a specific binding molecule-anti-CD3 fusion molecules may be in the range of 25 ng/kg to 50 µg/kg or 1 µg to 1 g. A physician will ultimately determine appropriate dosages to be used. An example of a suitable dosing regimen is provided in WO2017208018.

A single dose may be given. Alternatively multiple doses may be given, such as two or, more: or three or more doses. Where multiple doses are given the same dose may be given each time or a reduced dose may be given for the first and/or subsequent doses.

Specific binding molecules, pharmaceutical compositions, vectors, nucleic acids and cells of the invention may be provided in substantially pure form, for example, at least 80%, at least 85%, at least 90%, at least 91%, at least 92%, at least 93%, at least 94%, at least 95%, at least 96%, at least 97%, at least 98%, at least 99% or 100% pure.

Also provided by the invention are:
A specific binding molecule, nucleic acid, vector, pharmaceutical composition or cell of the invention for use in medicine, preferably in a human subject, preferably for use in a method of treating HIV infection or AIDS in a human subject.
the use of a specific binding molecule, nucleic acid, vector pharmaceutical composition or cell of the invention in the manufacture of a medicament for treating HIV infection or AIDS in a human subject.
a method of treating HIV infection or AIDS, comprising administering to a subject in need thereof a therapeutically effective amount of a specific binding molecule, nucleic acid, vector pharmaceutical composition or cell of the invention.
an injectable formulation for administering to a human subject comprising a specific binding molecule, nucleic acid, vector, pharmaceutical composition or cell of the invention.

The specific binding molecule, nucleic acid, vector, pharmaceutical composition or cell of the invention may be administered by injection or infusion. Particularly preferred is administration via intravenous infusion or subcutaneous injection. The human subject may be of the HLA-A*02 subtype.

The method of treatment may further include administering separately, in combination, or sequentially, one or more additional anti-viral agents and/or one or more additional immunotherapeutic agents and/or one of more soluble bispecific binding proteins. For example, the method of treatment may involve administration of two or more bispecific binding proteins, including the specific binding molecules of the invention and additional specific binding molecules that recognize alternative HIV proteins.

Patients to be treated may be receiving antiretroviral therapy (ART). Alternatively, patients to be treated may have ceased using ART, for example, such patients may be undergoing analytical therapy interruption (ATI). Alternatively, patients to treated may be ART naïve.

The terms "treatment," "treat," "treating." and the like, are meant to include slowing, stopping, or reversing the progression of HIV and/or AIDS. These terms also include alleviating, ameliorating, attenuating, eliminating, or reducing one or more symptoms of a disorder or condition, even if the disorder or condition is not actually eliminated and even if progression of the disorder or condition is not itself slowed, stopped or reversed.

"Therapeutically effective amount" means the amount of a compound, or pharmaceutically acceptable salt thereof, administered to the subject that will elicit the biological or medical response of or desired therapeutic effect on a subject.

A therapeutically effective amount can be readily determined by the attending clinician, as one skilled in the art, by the use of known techniques and by observing results obtained under analogous circumstances. In determining the effective amount for a subject, a number of factors are considered by the attending clinician, including, but not limited to: size, age, and general health: the specific disease or disorder involved: the degree of or involvement or the severity of the disease or disorder: the response of the individual subject; the particular compound administered: the mode of administration: the bioavailability characteristics of the preparation administered: the dose regimen selected: the use of concomitant medication; and other relevant circumstances.

Preferred features of each aspect of the invention are as for each of the other aspects mutatis mutandis. The prior art documents mentioned herein are incorporated by reference to the fullest extent permitted by law.

The invention is further described in the following non-limiting examples. Reference is made to the accompanying drawings.

EXAMPLES

Example 1—Identification of a Single TCR Alpha Chain Mutation that Results in Higher Yield without Negatively Impacting Binding Affinity for Target A bispecific molecule comprising a high affinity HIV TCR sequence, fused to an antiCD3 scFv was produced as previously described (Yang et al. *Mol Ther* 2016:24(11): 1913-1925: WO2017163064). The TCR end of the molecule recognizes the HLA-A*02 restricted 9-mer peptide, SLYNTVATL (SEQ ID NO 1), derived from the HIV Gag protein ($Gag_{78-85}$). The sequence of the TCR domain is shown in FIG. 1A (SEQ ID NOS: 33 and 34) and the full bispecific molecule is shown in FIG. 1B ((SEQ ID NOS: 35 and 36). During preclinical studies this molecule was found to have low yield when produced in *E. coli* (~1 mg/L). A production yield in this range was not considered suitable for manufacture of the reagent to support clinical development of the molecule. Attempts were made to improve yield through optimising refold and purification conditions using standard methods but were unsuccessful. Unexpectedly, a single mutation in the TCR alpha chain variable domain was found to increase yield without reducing binding affinity to the cognate pMHC target.

Methods

Single site mutagenesis was carried out to introduce an F to K mutation at position 50 of the TCR alpha chain variable domain, as indicated in the sequence shown in FIG. 2 (NB—in this example residue numbering is based on inclusion of a N terminal methionine). A bispecific protein containing this mutation was produced in *E. coli*. Yield and binding parameters of the mutant were compared to the corresponding non-mutated version.

Bispecific proteins were prepared as previously described. Briefly alpha and beta chains were expressed separately as inclusion bodies in the *E. coli* strain BL21-DE3(pLysS) by induction in mid-log phase with 0.5 mM IPTG. Inclusion bodies were isolated by sonication, followed by successive wash and centrifugation steps using 0.5% Triton X-100. Soluble protein was refolded by rapid dilution of a mixture of the dissolved α- and β-chain inclusion bodies into 5 M urea, 0.4 M L-arginine, 100 mM Tris pH 8.1, 3.7 mM cystamine, 6.6 mM b-mercapoethylamine. The refold mixture was dialysed for 24 h against 10 vol of demineralized water, then against 10 vol of 10 mM Tris pH 8.1. The refolded protein was filtered and purified through three sequentially chromatography steps—anion exchange (AIEX), cation exchange (CIEX) and size exclusion (SEC) pre-equilibrated in phosphate-buffered saline (PBS). Fractions comprising the main peak were pooled and analysed further. The final purified molecules were analysed by SDS-PAGE under reducing and non-reducing conditions. Yield and percentage of recovery were determined across all purification steps (AIEX, CIEX and SEC).

Purified bispecific molecules were subjected to surface plasmon resonance (SPR) analysis using a BIAcore® system as previously described (see for example Yang et al. *Mol Ther.* 2016: 24(11): 1913-1925: WO2017163064) to determine binding of the TCR end of the molecule to its target peptide HLA complex (SLYNTVATL (SEQ ID NO: 1) HLA-A*02). Briefly, biotinylated pHLAs were immobilised onto a streptavidin-coupled CM5 sensor chip. Flow cell one was loaded with free biotin alone to act as a control surface. $K_D$ values were calculated assuming Langmuir binding and data was analysed using a 1: 1 binding model (Biacore Insight Evaluation v2.0.15.12933 for single cycle kinetics analysis).

Results

Table A shows total yield and % recovery across all purification steps. FIG. 3 shows yield per volume of culture. For F50K, total yield and % recovery across all purification steps was substantially improved relative to the non-mutated (WT) version; in addition, yield per volume of culture showed a 4.5-fold improvement for F50K relative to wild type. Table B shows target binding parameters for each bispecific protein. These data show that F50K retained similar binding properties to the non-mutated WT protein, including $K_D$ and T1/2 ($K_D$=low pM and T1/2=>24 h).

Figure 4:
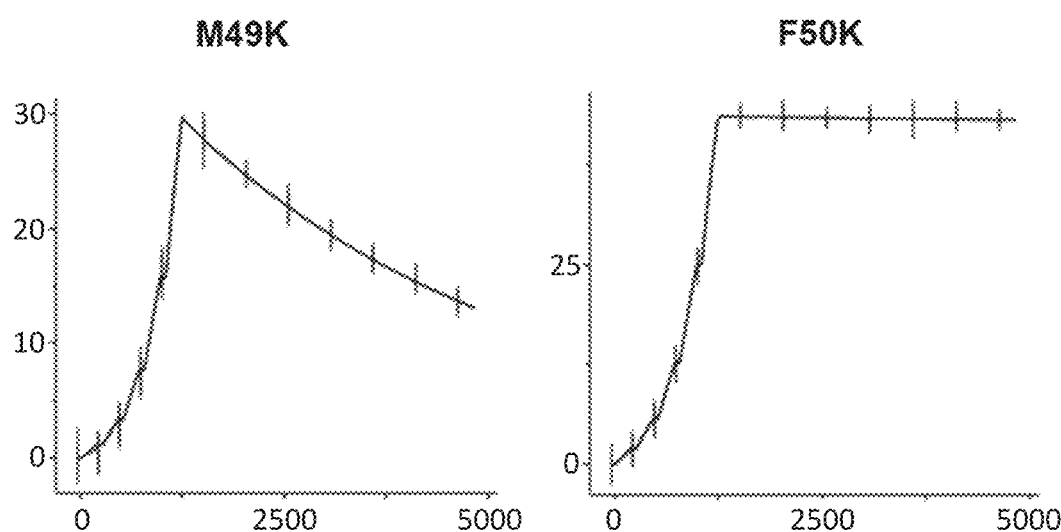
FIG. 4 shows graphs showing the binding kinetics for M49K and F50K mutants.

As a comparison, three further single site mutations (L47P, M49K, A53E) were made in the same region as F50 and tested using the same methods. As shown in Table A and FIG. 3, mutations L47P and A53E did not give rise to a substantial improvement in yield compared to F50K, whereas M49K showed a slightly higher improvement over F50K (4.9-fold). Interestingly, all three alternative mutations, including M49K, showed a substantial decrease in binding properties for the target relative to WT. FIG. 4 shows a side by side comparison of the binding kinetics for M49K and F50K.

TABLE A

Total yield and % recovery of bispecific protein following each chromatography step

| Bispecific protein | AIEX yield [mg] | AIEX % recovery | CIEX yield [mg] | CIEX % recovery | SEC yield [mg] | SEC % recovery |
|---|---|---|---|---|---|---|
| WT | 6.66 | 15.66% | 1.16 | 2.73% | 0.51 | 1.19% |
| L47P | 5.81 | 13.67% | 1.26 | 2.96% | 0.58 | 1.36% |
| M49K | 10.94 | 25.73% | 5.34 | 12.56% | 2.42 | 5.71% |
| F50K | 10.02 | 23.59% | 5.06 | 11.91% | 2.25 | 5.30% |
| A53E | 8.46 | 19.92% | 1.99 | 4.68% | 0.87 | 2.05% |

TABLE B

Binding parameters for each bispecific protein as determined by SPR

| Bispecific protein | $K_D$ (pM) | $k_a$ | $k_d$ | $t_{1/2}$ (h) | Rmax | SE(ka) (1/Ms) | SE(kd) (1/s) | Kinetics Chi$^2$ (RU$^2$) |
|---|---|---|---|---|---|---|---|---|
| WT | 15.2 | 7.41E+04 | 1.12E−06 | 171.2 | 83.3 | 4.92E+01 | 1.35E−08 | 9.92E−03 |
| L47P | 217 | 5.75E+04 | 1.25E−05 | 15.4 | 70.5 | 7.34E+01 | 2.10E−08 | 1.08E−02 |
| M49K | 3970 | 6.10E+04 | 2.42E−04 | 0.8 | 87.8 | 1.21E+02 | 1.83E−07 | 1.68E−02 |
| F50K | 28.2 | 9.39E+04 | 2.65E−06 | 72.7 | 84.3 | 4.07E+01 | 1.22E−08 | 1.15E−02 |
| A53E | 2590 | 3.39E+04 | 8.78E−05 | 2.2 | 55.6 | 1.03E+02 | 4.03E−08 | 5.72E−03 |

These data demonstrate the challenges of identifying bispecific proteins with improved developability. A single mutation in the TCR alpha chain variable domain (F50K) was shown to confer both improved yield and retain high affinity binding to target.

Example 2—Identification of an Additional TCR Alpha Chain Mutation that Increases Protein Stability without Negatively Impacting Binding Affinity for Target Further assessment of the F50K bispecific protein indicated that developability of the molecule may be impacted by reduced stability. Unexpectedly, a single mutation in the TCR alpha chain variable region was found to improve protein stability.

Methods

Single site mutagenesis was carried out to introduce an S to A mutation at position 96 of the TCR alpha chain variable domain, as indicated in FIG. 5 (NB—in this example residue numbering is based on the inclusion of an N terminal methionine). A bispecific protein containing this mutation was produced in E. coli and binding parameters analysed as previously described.

Analytical anion exchange chromatography (AIEX-UPLC) was used to assess protein stability following exposure to high pH (Tris pH9) for three days. Proteins were separated on an anion exchange UPLC column, eluted in order of increasing net surface negative charge, and detected by FLD detection (excitation 295 nm, emission 348 nm). Charge profile of the test sample was monitored by integrating the area under the curve of all peaks. The relative reduction in the main peak and corresponding increase in acidic species was used as a measure of stability. Deamidation was assessed using non-reducing peptide mapping. Briefly test sample and reference proteins were denatured and digested with a combination of Trypsin and LysC at +37° ° C. The resultant peptides were separated on a C18 HPLC column and detected by UV absorbance at 214 nm. Fragmentation spectra generated for each peptide were searched against a library of potential peptides based on the protein sequence, mass accuracy and potential modifications using PMI Byonic software.

Results

Table C shows target binding parameters. These data show that S96A gives similar target binding parameters compared to F50K alone. As a comparison, three alternative single site mutations were introduced in the same region of the protein as S96A. Of these, only T94L, but not N95Q or S96V resulted in similar target binding parameters compared to F50K alone.

TABLE C

Binding parameters for each bispecific protein as determined by SPR

| Bispecific protein | $K_D$ (pM) | ka | kd | tc | t ½ (h) | SE(ka) (1/Ms) | SE(kd) (1/s) | Rmax | Kinetics Chi$^2$ (RU$^2$) |
|---|---|---|---|---|---|---|---|---|---|
| F50K | 116 | 4.95E+04 | 5.75E−06 | 3.51E+12 | 34 | 9.17E+00 | 4.34E−09 | 116.7 | 1.99E−01 |
| F50K + T93L | 66 | 5.12E+04 | 3.37E−06 | 2.99E+12 | 57 | 1.59E+00 | 1.06E−10 | 104.1 | 1.90E−01 |
| F50K + N94Q | 3300 | 5.07E+04 | 1.68E−04 | 2.12E+12 | 1.2 | 9.36E+00 | 1.01E−08 | 111.5 | 1.79E−01 |
| F50K + S95A | 85 | 5.00E+04 | 4.25E−06 | 5.41E+10 | 45 | 4.70E+01 | 4.35E−09 | 117.4 | 2.07E−01 |
| F50K + S95V | 350 | 4.02E+04 | 1.41E−05 | 1.60E+12 | 14 | 6.45E+00 | 3.80E−09 | 111.2 | 1.23E−01 |

Table D summarises the results of AIEX-UPLC analysis. These data indicate that S96A is more stable than F50K alone or T94L. Further analysis of both S96A and T94L by peptide mapping indicated that increased stability is likely the result of reduced deamidation at position N95.

TABLE D

| | AE-UPLC analysis | | | | | |
|---|---|---|---|---|---|---|
| | % Relative | | | Change from T0 (sample %-T0) | | |
| Bispecific protein | Basic Peaks | Main Peak | Acidic Peaks | Basic Peaks | Main Peak | Acidic Peaks |
| F50K (ref) | 0 | 85.4 | 14.5 | 0 | 36.5 | −36.5 |
| F50K (high pH) | 0 | 48.9 | 51 | | | |
| F50K + T93L (ref) | 0.1 | 76.9 | 23 | 0.1 | 36.5 | −36.5 |
| F50K + T93L (high pH) | 0 | 40.4 | 59.5 | | | |
| F50K + S95A (ref) | 0.1 | 76.3 | 23.6 | 0.1 | 29.4 | −29.5 |
| F50K + S95A (high pH) | 0 | 46.9 | 53.1 | | | |

TABLE E

| Peptide mapping | | | |
|---|---|---|---|
| | | % deamidation of N94 | |
| Alpha chain | αCDR3 | Control | High pH |
| F50K | CAVRTNSGYALNF (SEQ ID NO: 38) | 1.08 | 16.7 |
| F50K + S95A | CAVRTNAGYALNF (SEQ ID NO: 39) | 0.17 | 6.07 |

Example 3—Improved Bispecific Molecule Recognizes Common Viral Escape Variants and Demonstrates Potent and Specific of Killing of HIV Infected Cells A bispecific protein incorporating F50K+S96A was further analysed to assess further properties, including recognition of common viral escape variants and potency against antigen positive cell lines. In this example, the TCR was fused to an alternative antiCD3 domain, which is further described in WO2020157210. The full sequence of the bispecific molecule is shown in FIG. 6.

Methods

SPR analysis was performed on a Biacore instrument as previously described. Briefly, variants of the HIV peptide listed in this were complexed in a soluble format with HLAA*02:01; these biotinylated complexes were then immobilised onto a Biacore CM5 chip preloaded with streptavidin. Soluble bispecific protein was injected at 5 increasing concentrations onto the immobilised pHLA. After the fifth injection, dissociation was measured for 2 hours. The association and dissociation of the molecule from each HLA complex was measured using the Biacore instrument. The relative half-life for each interaction was calibrated against index peptide in HLAA*02:01.

Potency was determined using the cytokine enzyme-linked immunosorbent spot (ELISPOT) assay to detect interferon gamma (IFN-γ) or granzyme B (GrB) secreted by T cells upon activation. The HLAA*02:01 lymphoma-derived cancer cell line, T2, pulsed with the HIV Gag$_{77-85}$ peptide, and a peptide-pulsed HLAA*02:01/B2m transduced T cell line (C8166 A2B2M), were used as target cells for IFN-γ and GrB assays respectively. PBMCs obtained from HIV-naïve donors were used as the effectors. Cytokine release (IFN-γ) was used to measure T cell activation, and GrB release was used as a surrogate for T cell-mediated target cell killing. Target cells were incubated with PBMCs from different HIV-naïve donors (CTL013, CTL014, CTL018, SC009, SC001B) and increasing concentrations of IMCM113V, overnight (IFN-γ-specific, top) or for 4048 hours (GrB-specific, bottom).

Results

Table F shows that the bispecific protein bound each of the variant peptides tested with affinities (K$_D$) in the low nanomolar to picomolar range, and with half-lives (t1/2) of several hours. Whilst there was a reduction in affinity against the variants, in particular those containing the Y3F and T8V substitutions, the weakest interaction (Y3F T8V) between IMCM113V and peptide HLA complex was still considered to be very strong, relative to a wild-type TCR. These data demonstrate the bispecific protein strongly recognizes common escape variants.

TABLE F

| Binding parameters of bispecific protein to peptide variants | | | | | | | |
|---|---|---|---|---|---|---|---|
| Peptide Sequence | SEQ ID NO: | Variant Name | ka (1/Ms) | kd (1/s) | KD (M) | t$_{1/2}$ (h) | t$_{1/2}$ relative to index |
| SLYNTVATL | 1 | Wild type | 6.04E+04 | 5.79E-06 | 9.59E-11 | 33.33 | 1.00 |
| SLYNTIAVL | 12 | V6I T8V | 5.12E+04 | 8.40E-06 | 1.64E-10 | 22.92 | 0.69 |
| SLYNTIATL | 11 | V6I | 5.84E+04 | 1.15E-05 | 1.97E-10 | 16.72 | 0.50 |
| SLFNTIATL | 13 | Y3F V6I | 3.76E+04 | 2.38E-05 | 6.32E-10 | 8.08 | 0.24 |
| SLFNTIAVL | 14 | Y3F V6I T8V | 5.81E+04 | 2.72E-05 | 4.68E-10 | 7.08 | 0.21 |
| SLYNTVAVL | 40 | T8V | 6.04E+04 | 3.44E-05 | 5.69E-10 | 5.58 | 0.17 |

TABLE F-continued

Binding parameters of bispecific protein to peptide variants

| Peptide Sequence | SEQ ID NO: | Variant Name | ka (1/Ms) | kd (1/s) | KD (M) | $t_{1/2}$ (h) | $t_{1/2}$ relative to index |
|---|---|---|---|---|---|---|---|
| SLFNTVATL | 6 | Y3F | 3.78E+04 | 4.96E-05 | 1.31E-09 | 3.89 | 0.12 |
| SLFNTVAVL | 7 | Y3F T8V | 3.93E+04 | 6.36E-05 | 1.62E-09 | 3.03 | 0.09 |

Figure 7:
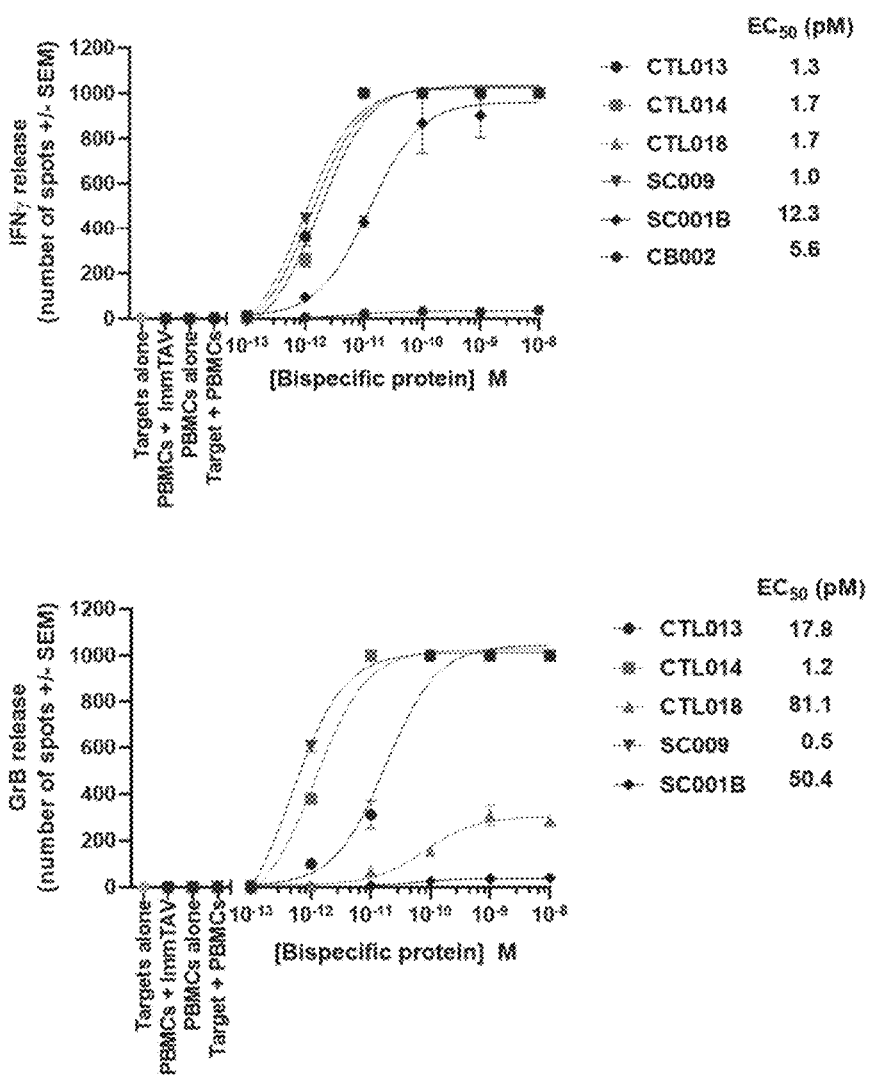
FIG. 7 shows graphs showing the potency of T cell redirection as determined by IFNy (upper) and GrB (lower) release.

FIG. 7 demonstrates that the bispecific protein redirected effector T cells to release IFN-γ and GrB in a dose-dependent manner, when cultured with HLAA*02:01-positive peptide (HIV Gag$_{77-85}$)-pulsed T2 and C8166 A2B2M target cells. The EC50 values obtained from the responsive donors are indicated on the graphs and ranged from 1.0 to 12.3 pM for IFN-γ release and from 0.5-81.1 pM for GrB release. These data indicate that the bispecific protein can specifically redirect T cell activity in the presence of HLAA*02:01-positive Gag$_{77-85}$ positive cells to activate T cells, resulting in dose-dependent cytokine release, with potency in the low picomolar range.

EMBODIMENTS

Embodiment 1. A specific binding molecule having the property of binding to SLYNTVATL (SEQ ID NO: 1) in complex with HLA-A*02 and comprising a TCR alpha chain variable domain and a TCR beta chain variable domain,
wherein the alpha chain variable domain comprises an amino acid sequence selected from:

a)
```
                                          (SEQ ID NO: 2)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNSGYALN FGKGTSLLVT P;
``` b)
```
                                          (SEQ ID NO: 3)
AKEVEQNSGP LSVPEGAIAS LNCTYSSWEG QSFFWYRQYS

GKSPELIMFL YADPDKEDGR FTAQLNKASQ YVSLLIRDSQ

PSDSATYLCA VRTNAGYALN FGKGTSLLVT P;
or
``` c)
```
                                          (SEQ ID NO: 4)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNAGYALN FGKGTSLLVT P;
``` optionally with an N-terminal methionine (SEQ ID NOs: 41-43), and
the beta chain variable domain comprises the amino acid sequence:

```
                                          (SEQ ID NO: 5)
DAGVTQSPTH LIKTRGQQVT LRCSPKSGHD TVSWYQQALG

QGPQFIFQAV RGVERQRGNF PDRFSGHQFP NYSSELNVNA

LLLGDSALYL CASSDTVSYE QYFGPGTRLT VT_,
``` optionally with an N-terminal methionine (SEQ ID NO: 44).

Embodiment 2. The specific binding molecule of embodiment 1, wherein the alpha chain variable domain comprises the amino acid sequence:

```
                                          (SEQ ID NO: 2)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNSGYALN FGKGTSLLVT P
```

Embodiment 3. The specific binding molecule of embodiment 1, wherein the alpha chain variable domain comprises the amino acid sequence:

```
                                          (SEQ ID NO: 3)
AKEVEQNSGP LSVPEGAIAS LNCTYSSWEG QSFFWYRQYS

GKSPELIMFL YADPDKEDGR FTAQLNKASQ YVSLLIRDSQ

PSDSATYLCA VRTNAGYALN FGKGTSLLVT P
```

Embodiment 4. The specific binding molecule of embodiment 1, wherein the alpha chain variable domain comprises the amino acid sequence:

```
                                          (SEQ ID NO: 4)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNAGYALN FGKGTSLLVT P
```

Embodiment 5. The specific binding molecule of any of embodiments 1-4, wherein the alpha chain variable domain amino acid sequence comprises one or more of the following mutations, numbered according to SEQ ID NO: 43:
A2Q
V73I
Q81K
P82L.

Embodiment 6. The specific binding molecule of any of embodiments 1-5, which is an alpha-beta heterodimer, having an alpha chain TRAC constant domain and a beta chain TRBC1 or TRBC2 constant domain.

Embodiment 7. The specific binding molecule of embodiment 6, wherein the alpha and beta chain constant domain amino acid sequences are modified by truncation or substitution to delete the native disulfide bond between Cys4 of exon 2 of TRAC and Cys2 of exon 2 of TRBC1 or TRBC2.

Embodiment 8. The specific binding molecule of embodiment 6 or embodiment 7, wherein the alpha and beta chain constant domain amino acid sequence(s) are modified by substitution of cysteine residues for Thr 48 of TRAC and Ser 57 of TRBC1 or TRBC2, the said cysteines forming a disulfide bond between the TCR alpha and beta constant domains.

Embodiment 9. The specific binding molecule of any of embodiments 1-8, which is in single chain format of the type Vα-L-Vβ, Vβ-L-Vα, Vα-Cα-L-Vβ, Vα-L-Vβ-CB, Vα-Cα-L-Vβ-Cβ or Vβ-Cβ-L-Vα-Cα wherein Vα and Vβ are TCR alpha and beta variable regions respectively, Cα and Cβ are TCR α and β constant regions respectively, and L is a linker sequence.

Embodiment 10. The specific binding molecule of any of embodiments 1-9, which is associated with a detectable label, a therapeutic agent, or a PK modifying moiety.

Embodiment 11. The specific binding molecule of any of embodiments 1-10, which is associated with an anti-CD3 antibody covalently linked to the C- or N-terminus of the TCR alpha or beta chain.

Embodiment 12. The specific binding molecule of embodiment 11, wherein the anti-CD3 antibody is covalently linked to the C- or N-terminus of the TCR beta chain via a linker sequence.

Embodiment 13. The specific binding molecule of embodiment 12, wherein the linker sequence is selected from the group consisting of GGGGS (SEQ ID NO: 16), GGGSG (SEQ ID NO: 17), GGSGG (SEQ ID NO: 18), GSGGG (SEQ ID NO: 19), GSGGGP (SEQ ID NO: 20), GGEPS (SEQ ID NO: 21), GGEGGGP (SEQ ID NO: 22), and GGEGGGSEGGGS (SEQ ID NO: 23).

Embodiment 14. The specific binding molecule of embodiment 12 or embodiment 13, wherein the beta chain comprises the amino acid sequence:

```
                            (SEQ ID NO: 30)
AIQMTQSPS SLSASVGDRV TITCRASQDI RNYLNWYQQK

PGKAPKLLIY YTSRLESGVP SRFSGSGSGT DYTLTISSLQ

PEDFATYYCQ QGNTLPWTFG QGTKVEIKGG GGSGGGGSGG

GGSGGGGSGG GSEVQLVESG GGLVQPGGSL RLSCAASGYS

FTGYAMNWVR QAPGKGLEWV ALINPYKGVS TYNQKFKDRF

TFSVDKSKNT AYLQMNSLRA EDTAVYYCAR SGYYGDSDWY

FDVWGQGTLV TVSSGGGGSD AGVTQSPTHL IKTRGQQVTL

RCSPKSGHDT VSWYQQALGQ GPQFIFQAVR GVERQRGNFP

DRFSGHQFPN YSSELNVNAL LLGDSALYLC ASSDTVSYEQ

YFGPGTRLTV TEDLKNVFPP EVAVFEPSEA EISHTQKATL

VCLATGFYPD HVELSWWVNG KEVHSGVCTD PQPLKEQPAL

NDSRYALSSR LRVSATFWQD PRNHFRCQVQ FYGLSENDEW

TQDRAKPVTQ IVSAEAWGRA D
```

Embodiment 15. The specific binding molecule of embodiment 12 or embodiment 13, wherein the beta chain comprises the amino acid sequence:

```
                            (SEQ ID NO: 31)
AIQMTQSPS SLSASVGDRV TITCRASQDI RNYLNWYQQK

PGKAPKLLIY YTSRLESGVP SRFSGSGSGT DYTLTISSLQ

PEDFATYYCQ QGNTLPWTFG QGTKVEIKGG GGSGGGGSGG

GGSGGGGSGG GSEVQLVESG GGLVQPGGSL RLSCAASGYS

FTGYTMNWVR QAPGKGLEWV ALINPYKGVS TYNQKFKDRF

TISVDKSKNT AYLQMNSLRA EDTAVYYCAR SGYYGDSDWY

FDVWGQGTLV TVSSGGGGSD AGVTQSPTHL IKTRGQQVTL

RCSPKSGHDT VSWYQQALGQ GPQFIFQAVR GVERQRGNFP

DRFSGHQFPN YSSELNVNAL LLGDSALYLC ASSDTVSYEQ

YFGPGTRLTV TEDLKNVFPP EVAVFEPSEA EISHTQKATL

VCLATGFYPD HVELSWWVNG KEVHSGVCTD PQPLKEQPAL

NDSRYALSSR LRVSATFWQD PRNHFRCQVQ FYGLSENDEW

TQDRAKPVTQ IVSAEAWGRA D
```

Embodiment 16. The specific binding molecule of embodiment 14 or embodiment 15, wherein the alpha chain comprises the amino acid sequence:

```
                            (SEQ ID NO: 32)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNAGYALN FGKGTSLLVT PHIQKPDPAV

YQLRDSKSSD KSVCLFTDFD SQTNVSQSKD SDVYITDKCV

LDMRSMDFKS NSAVAWSNKS DFACANAFNN SIIPEDT
```

Embodiment 17. A nucleic acid molecule encoding a TCR alpha chain and/or a TCR beta chain as defined in any of embodiments 1-16.

Embodiment 18. An expression vector comprising the nucleic acid of embodiment 17.

Embodiment 19. A cell harbouring (a) a TCR expression vector which comprises nucleic acid as in embodiment 17 in a single open reading frame, or two distinct open reading frames encoding the alpha chain and the beta chain respectively: or (b) a first expression vector which comprises nucleic acid encoding the alpha chain of a TCR as in any one of embodiments 1 to 16 and a second expression vector which comprises nucleic acid encoding the beta chain of a TCR as in any one of embodiments 1 to 16.

Embodiment 20. An isolated or non-naturally occurring cell, especially a T-cell, presenting a TCR as claimed in any one of embodiments 1 to 10.

Embodiment 21. A pharmaceutical composition comprising a specific binding molecule as claimed in any one of embodiments 1 to 16, a nucleic acid as claimed in embodiment 17, a vector as in embodiment 18 and/or a cell as embodiment 19 or embodiment 20, together with one or more pharmaceutically acceptable carriers or excipients.

Embodiment 22. The specific binding molecule of any one of embodiments 1 to 16, a nucleic acid as in embodiment 17, vector as in embodiment 18 and/or cell of embodiment 19 or embodiment 20 for use in medicine, in a human subject.

Embodiment 23. The specific binding molecule of any one of embodiments 1 to 16, a nucleic acid as in embodiment 17, vector as claimed in embodiment 18 and/or cell of embodiment 19 or embodiment 20 for use in a method of treating HIV infection or AIDS in a human subject.

Embodiment 24. A method of treating HIV infection or AIDS in a human subject, comprising administering a therapeutically effective amount of a specific binding molecule of any one of embodiments 1 to 16.

The invention claimed is:

1. A specific binding molecule having the property of binding to SLYNTVATL (SEQ ID NO: 1) in complex with HLA-A*02 and comprising a TCR alpha chain variable domain and a TCR beta chain variable domain,
   wherein the alpha chain variable domain comprises an amino acid sequence selected from:

a)
   (SEQ ID NO: 2)
   AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNSGYALN FGKGTSLLVT P;

b)
   (SEQ ID NO: 3)
   AKEVEQNSGP LSVPEGAIAS LNCTYSSWEG QSFFWYRQYS

GKSPELIMFL YADPDKEDGR FTAQLNKASQ YVSLLIRDSQ

PSDSATYLCA VRTNAGYALN FGKGTSLLVT P;
   and c)
   (SEQ ID NO: 4)
   AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNAGYALN FGKGTSLLVT P;

optionally with an N-terminal methionine (SEQ ID NOs: 41-43), and the beta chain variable domain comprises the amino acid sequence:

(SEQ ID NO: 5)
   DAGVTQSPTH LIKTRGQQVT LRCSPKSGHD TVSWYQQALG

QGPQFIFQAV RGVERQRGNF PDRFSGHQFP NYSSELNVNA

LLLGDSALYL CASSDTVSYE QYFGPGTRLT VT, optionally with an N-terminal methionine (SEQ ID NO: 44).

2. The specific binding molecule as claimed in claim 1, wherein the alpha chain variable domain comprises the amino acid sequence:

```
                                            (SEQ ID NO: 2)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNSGYALN FGKGTSLLVT P.
```

3. The specific binding molecule as claimed in claim 1, wherein the alpha chain variable domain comprises the amino acid sequence:

```
                                            (SEQ ID NO: 3)
AKEVEQNSGP LSVPEGAIAS LNCTYSSWEG QSFFWYRQYS

GKSPELIMFL YADPDKEDGR FTAQLNKASQ YVSLLIRDSQ

PSDSATYLCA VRTNAGYALN FGKGTSLLVT P.
```

4. The specific binding molecule as claimed in claim 1, wherein the alpha chain variable domain comprises the amino acid sequence:

```
                                            (SEQ ID NO: 4)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNAGYALN FGKGTSLLVT P.
```

5. The specific binding molecule as claimed in claim 1, which is an alpha-beta heterodimer, having an alpha chain TRAC constant domain and a beta chain TRBC1 or TRBC2 constant domain.

6. The specific binding molecule as claimed in claim 5, wherein the alpha and beta chain constant domain amino acid sequences are modified by truncation or substitution to delete the native disulfide bond between Cys4 of exon 2 of TRAC and Cys2 of exon 2 of TRBC1 or TRBC2.

7. The specific binding molecule as claimed in claim 6, wherein the alpha and beta chain constant domain amino acid sequence(s) are modified by substitution of cysteine residues for Thr 48 of TRAC and Ser 57 of TRBC1 or TRBC2, the said cysteines forming a disulfide bond between the TCR alpha and beta constant domains.

8. The specific binding molecule as claimed in claim 1, which is in single chain format of the type Vα-L-Vβ, Vβ-L-Vα, Vα-Cα-L-Vβ, Vα-L-Vβ-Cβ, Vα-Cα-L-Vβ-CB or Vβ-Cβ-L-Vα-Cα wherein Vα and Vβ are TCR alpha and beta variable regions respectively, Cα and Cβ are TCR α and β constant regions respectively, and L is a linker sequence.

9. The specific binding molecule as claimed in claim 1, which is associated with a detectable label, a therapeutic agent, or a PK modifying moiety.

10. The specific binding molecule as claimed in claim 9, which is associated with an anti-CD3 antibody covalently linked to the C- or N-terminus of the TCR alpha or beta chain.

11. The specific binding molecule as claimed in claim 10, wherein the anti-CD3 antibody is covalently linked to the C- or N-terminus of the TCR beta chain via a linker sequence.

12. The specific binding molecule as claimed in claim 11, wherein the linker sequence is selected from the group consisting of GGGGS (SEQ ID NO: 16), GGGSG (SEQ ID NO: 17), GGSGG (SEQ ID NO: 18), GSGGG (SEQ ID NO: 19), GSGGGP (SEQ ID NO: 20), GGEPS (SEQ ID NO: 21), GGEGGGP (SEQ ID NO: 22), and GGEGGGSEGGGS (SEQ ID NO: 23).

13. The specific binding molecule as claimed in claim 12, wherein the beta chain comprises the amino acid sequence:

```
                                            (SEQ ID NO: 30)
AIQMTQSPS SLSASVGDRV TITCRASQDI RNYLNWYQQK

PGKAPKLLIY YTSRLESGVP SRFSGSGSGT DYTLTISSLQ

PEDFATYYCQ QGNTLPWTFG QGTKVEIKGG GGSGGGGSGG

GGSGGGGSGG GSEVQLVESG GGLVQPGGSL RLSCAASGYS

FTGYAMNWVR QAPGKGLEWV ALINPYKGVS TYNQKFKDRF

TFSVDKSKNT AYLQMNSLRA EDTAVYYCAR SGYYGDSDWY

FDVWGQGTLV TVSSGGGGSD AGVTQSPTHL IKTRGQQVTL

RCSPKSGHDT VSWYQQALGQ GPQFIFQAVR GVERQRGNFP

DRFSGHQFPN YSSELNVNAL LLGDSALYLC ASSDTVSYEQ

YFGPGTRLTV TEDLKNVFPP EVAVFEPSEA EISHTQKATL

VCLATGFYPD HVELSWWVNG KEVHSGVCTD PQPLKEQPAL

NDSRYALSSR LRVSATFWQD PRNHFRCQVQ FYGLSENDEW

TQDRAKPVTQ IVSAEAWGRA D.
```

14. The specific binding molecule as claimed in claim 12, wherein the beta chain comprises the amino acid sequence:

```
                                            (SEQ ID NO: 31)
AIQMTQSPS SLSASVGDRV TITCRASQDI RNYLNWYQQK

PGKAPKLLIY YTSRLESGVP SRFSGSGSGT DYTLTISSLQ

PEDFATYYCQ QGNTLPWTFG QGTKVEIKGG GGSGGGGSGG

GGSGGGGSGG GSEVQLVESG GGLVQPGGSL RLSCAASGYS

FTGYTMNWVR QAPGKGLEWV ALINPYKGVS TYNQKFKDRF

TISVDKSKNT AYLQMNSLRA EDTAVYYCAR SGYYGDSDWY

FDVWGQGTLV TVSSGGGGSD AGVTQSPTHL IKTRGQQVTL

RCSPKSGHDT VSWYQQALGQ GPQFIFQAVR GVERQRGNFP

DRFSGHQFPN YSSELNVNAL LLGDSALYLC ASSDTVSYEQ

YFGPGTRLTV TEDLKNVFPP EVAVFEPSEA EISHTQKATL

VCLATGFYPD HVELSWWVNG KEVHSGVCTD PQPLKEQPAL

NDSRYALSSR LRVSATFWQD PRNHFRCQVQ FYGLSENDEW

TQDRAKPVTQ IVSAEAWGRA D.
```

15. The specific binding molecule as claimed in claim 13, wherein the alpha chain comprises the amino acid sequence:

```
                                            (SEQ ID NO: 32)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNAGYALN FGKGTSLLVT PHIQKPDPAV

YQLRDSKSSD KSVCLFTDFD SQTNVSQSKD SDVYITDKCV

LDMRSMDFKS NSAVAWSNKS DFACANAFNN SIIPEDT.
```

16. A pharmaceutical composition comprising a specific binding molecule having the property of binding to SLYNTVATL (SEQ ID NO: 1) in complex with HLA-A*02 and comprising a TCR alpha chain variable domain and a TCR beta chain variable domain, wherein the alpha chain variable domain amino acid sequence comprises an amino acid sequence selected from:

a)
```
                                        (SEQ ID NO: 2)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNSGYALN FGKGTSLLVT P;
``` b)
```
                                        (SEQ ID NO: 3)
AKEVEQNSGP LSVPEGAIAS LNCTYSSWEG QSFFWYRQYS

GKSPELIMFL YADPDKEDGR FTAQLNKASQ YVSLLIRDSQ

PSDSATYLCA VRTNAGYALN FGKGTSLLVT P;
and
``` c)
```
                                        (SEQ ID NO: 4)
AKEVEQNSGP LSVPEGAIAS LNCTYSSWEG QSFFWYRQYS

GKSPELIMKL YADPDKEDGR FTAQLNKASQ YVSLLIRDSQ

PSDSATYLCA VRTNAGYALN FGKGTSLLVT P;
``` optionally with an N-terminal methionine (SEQ ID NOs: 41-43), and the beta chain variable domain comprises the amino acid sequence:

```
                                        (SEQ ID NO: 5)
DAGVTQSPTH LIKTRGQQVT LRCSPKSGHD TVSWYQQALG

QGPQFIFQAV RGVERQRGNF PDRFSGHQFP NYSSELNVNA

LLLGDSALYL CASSDTVSYE QYFGPGTRLT VT,
``` optionally with an N-terminal methionine (SEQ ID NO: 44), together with one or more pharmaceutically acceptable carriers or excipients.

\* \* \* \* \*

UNITED STATES PATENT AND TRADEMARK OFFICE
CERTIFICATE OF CORRECTION

| | | |
|---|---|---|
| PATENT NO. | : 12,103,971 B2 | Page 1 of 1 |
| APPLICATION NO. | : 17/938321 | |
| DATED | : October 1, 2024 | |
| INVENTOR(S) | : Dembek et al. | |

It is certified that error appears in the above-identified patent and that said Letters Patent is hereby corrected as shown below:

On the Title Page

Item (56), in Column 2, under "OTHER PUBLICATIONS", Line 3, delete "the a" and insert -- the α --, therefor.

In the Claims

In Column 53, in Claim 8, Line 50, delete "Vα-Cα-L-Vβ-CB" and insert -- Vα-Cα-L-Vβ-Cβ --, therefor.

Signed and Sealed this
Eleventh Day of February, 2025

Coke Morgan Stewart
*Acting Director of the United States Patent and Trademark Office*